United States Patent
Gee et al.

(10) Patent No.: US 8,492,129 B2
(45) Date of Patent: Jul. 23, 2013

(54) PRODUCTION OF CONJUGATES

(75) Inventors: Nicholas Gee, Cambridge (GB); Michael Knowles, Cambridge (GB)

(73) Assignee: Innova Biosciences, Ltd., Cambridge (GB)

( * ) Notice: Subject to any disclaimer, the term of this patent is extended or adjusted under 35 U.S.C. 154(b) by 894 days.

(21) Appl. No.: 12/096,000

(22) PCT Filed: Dec. 12, 2006

(86) PCT No.: PCT/GB2006/004633
§ 371 (c)(1),
(2), (4) Date: Jun. 3, 2008

(87) PCT Pub. No.: WO2007/068906
PCT Pub. Date: Jun. 21, 2007

(65) Prior Publication Data
US 2008/0299637 A1    Dec. 4, 2008

(30) Foreign Application Priority Data

Dec. 12, 2005 (GB) .................................... 0525223.4
Jul. 21, 2006 (GB) .................................... 0614533.8

(51) Int. Cl.
*C12N 11/00* (2006.01)
*C12N 11/02* (2006.01)

(52) U.S. Cl.
USPC ........................................ 435/177; 435/174

(58) Field of Classification Search
USPC ................................................. 435/174, 177
See application file for complete search history.

(56) References Cited

U.S. PATENT DOCUMENTS
2006/0147476 A1*   7/2006 Schofield .................. 424/268.1

FOREIGN PATENT DOCUMENTS
WO    WO 03/015757    2/2003

OTHER PUBLICATIONS

Pierce Handbook and General Calalog. 1989. Protein modification Reagents, p. 220.*
Lillo et al. (A Human Single-Chain Antibody Specific for Integrin α3β1 Capable of Cell Internalization and Delivery of Antitumor Agents. Chemistry and Biology. 2004. 11:897-906).*
Pierce Catalog (Pierce 1989 Handbook and General Catalog, p. 220).*
Mattson et al. (A practical approach to crosslinking. Molecular Biology Reports. 1993. 17: 167-183.*
Inoue et al. "beta-Glycosylamidine as a ligand for affinity chromatography tailored to the glycon substrate specificity of beta-glycosidases." Carbohydrate Res. 338: 1477-1490, 2003.
Manjula et al. "Conjugation of multiple copies of polyethylene glycol to hemoglobin facilitated through thiolation: Influence on hemoglobin structure and function." The Protein Journal (formerly J. Prot. Chem.) 24: 133-146, 2005.
McCall et al. "Simplified method for conjugating macrocyclic bifunctional chelating agents to antibodies via 2 iminothiolane." Bioconjugate Chem. 1: 222-226, 1990.

* cited by examiner

*Primary Examiner* — Karen Cochrane Carlson
*Assistant Examiner* — Natalie Moss
(74) *Attorney, Agent, or Firm* — Morgan, Lewis & Bockius LLP

(57) ABSTRACT

A method of reacting a first chemical entity and a second chemical entity to form a conjugate in which the first and second chemical entities are covalently bound with respect to each other, comprises bringing into simultaneous contact the first chemical entity, the second chemical entity and a thiol generator, wherein the thiol generator reacts with the first chemical entity in a thiolation reaction resulting in formation of a free sulfhydryl group on the first chemical entity, and the free sulfhydryl group reacts with the second chemical entity to form the conjugate, and wherein the second chemical entity is polyvalent with respect to its reactivity with sulfhydryl groups. The present invention primarily differs from the prior art in that no separation step is involved between reaction of the thiol generator and first chemical entity and reaction with the second chemical entity. The invention also provides a conjugation kit.

27 Claims, 8 Drawing Sheets

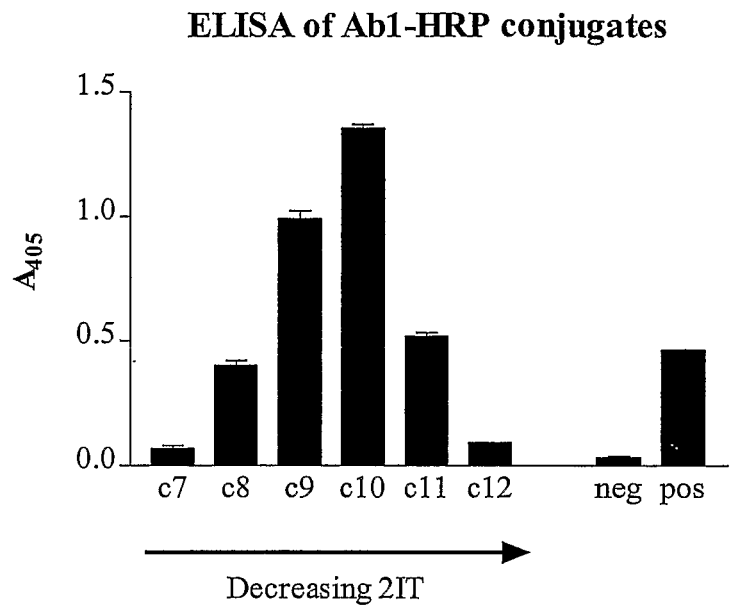
FIG. 1 (Example 4)
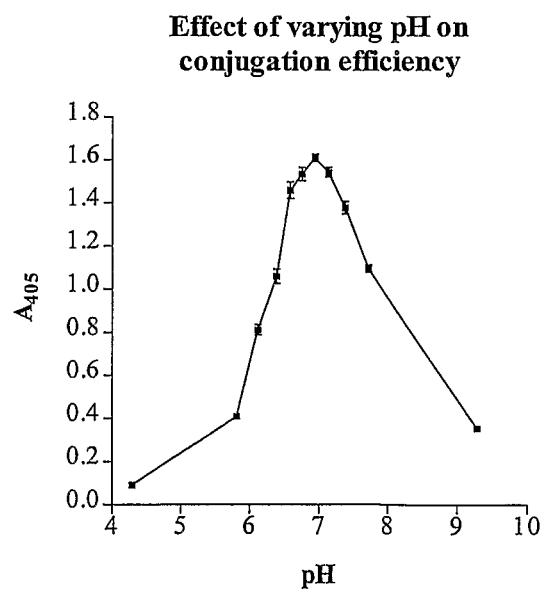
FIG. 2 (Example 5)

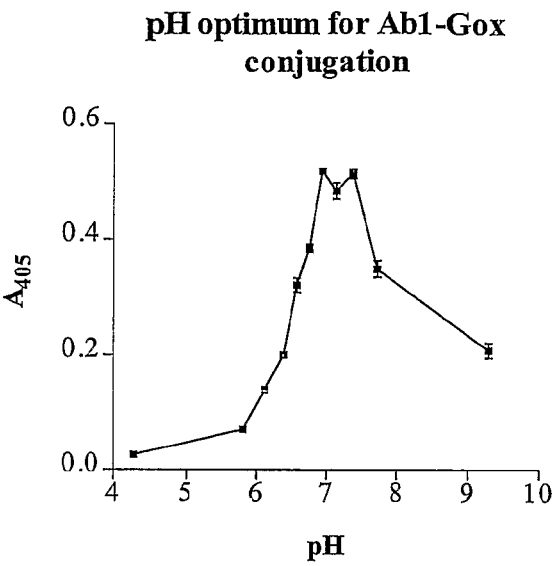
FIG. 3 (Example 6)
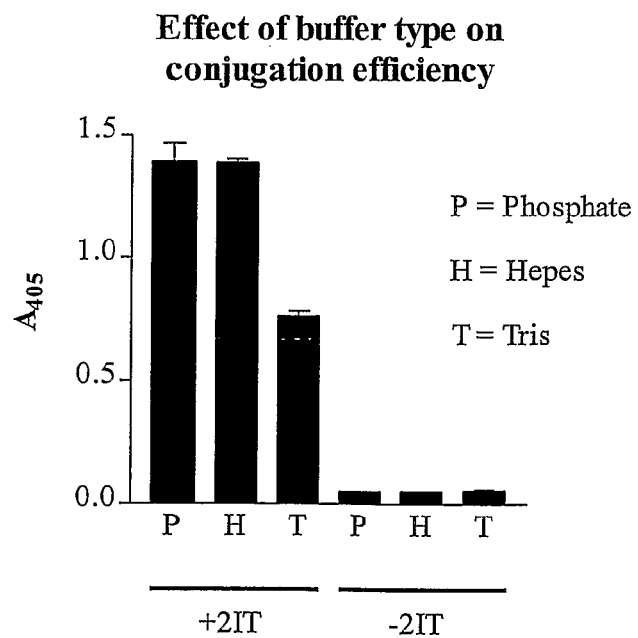
FIG. 4 (Example 7)

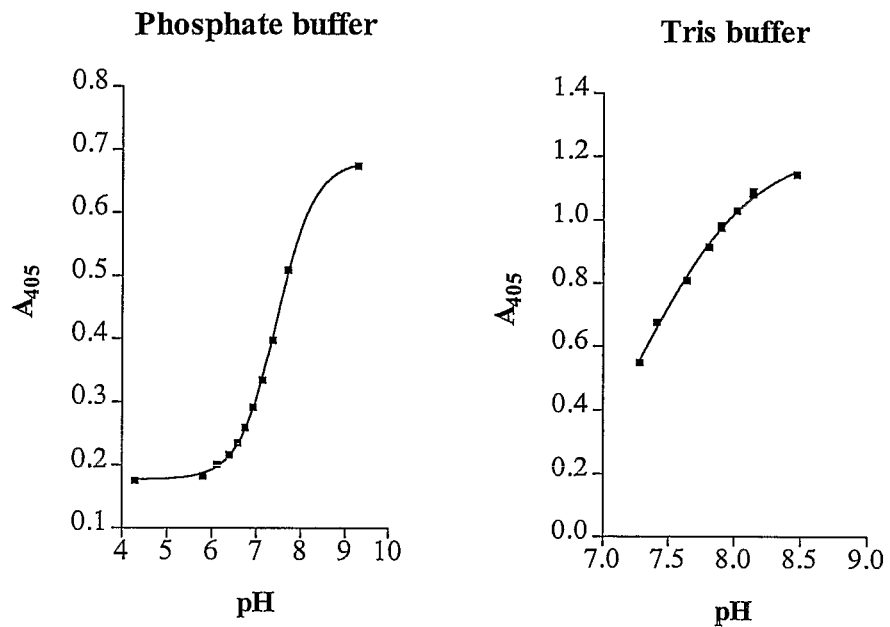
FIG. 5 (Example 8)
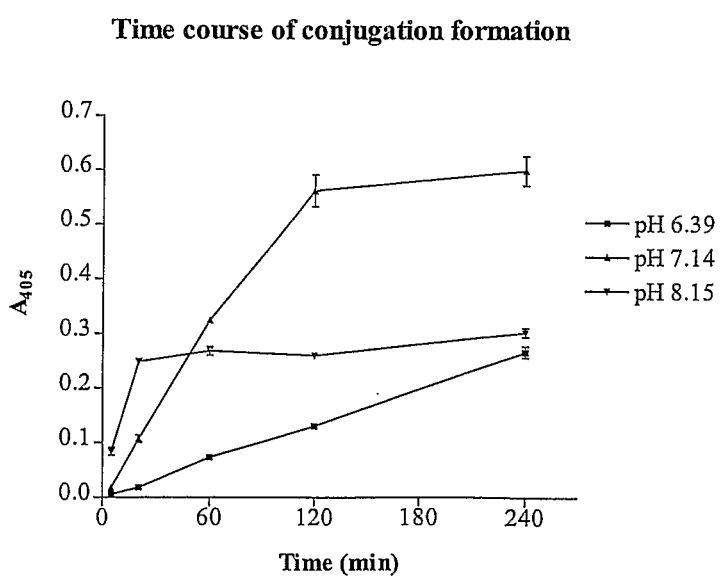
FIG. 6 (Example 9)

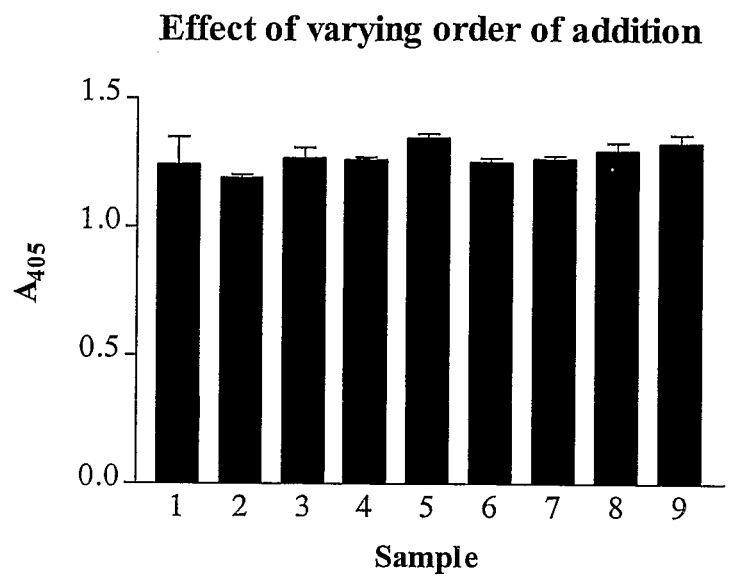
FIG. 7 (Example 10)
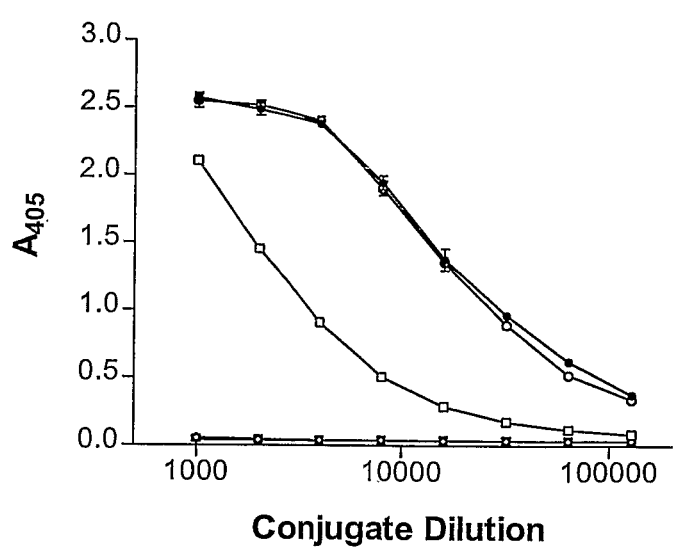
FIG. 8 (Example 12)

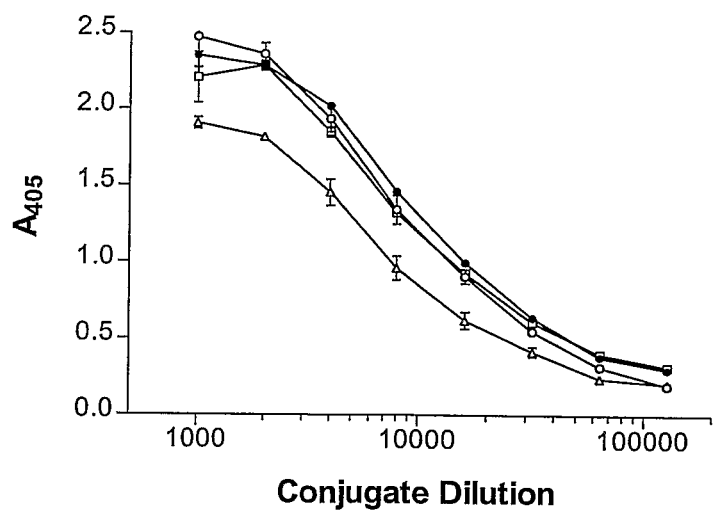
FIG. 9 (Example 13)
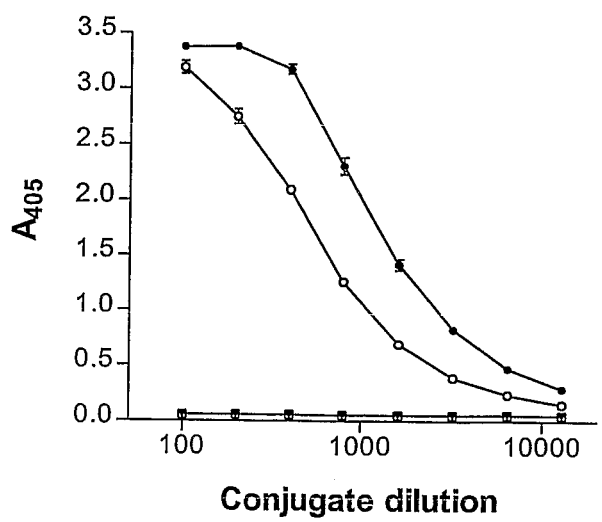
FIG. 10 (Example 14)

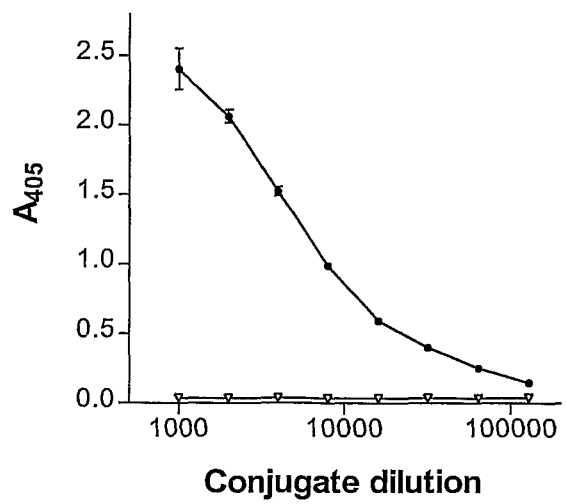
FIG 11 (Example 15)
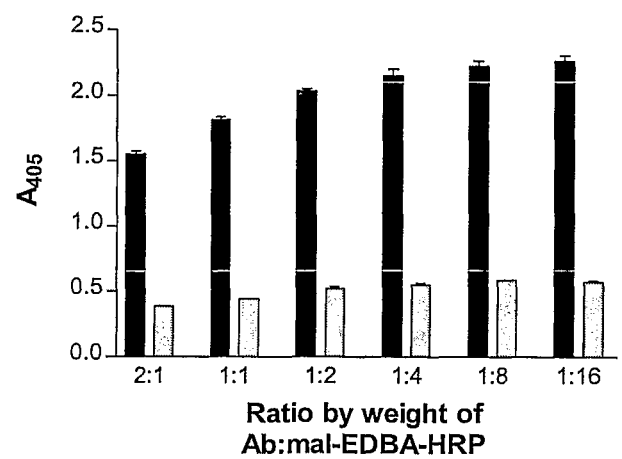
FIG 12 (Example 16)

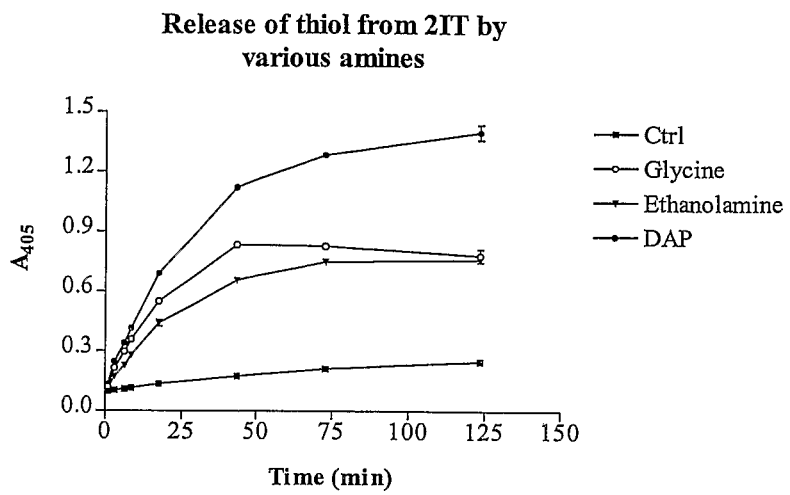
FIG. 13 (Example 17)
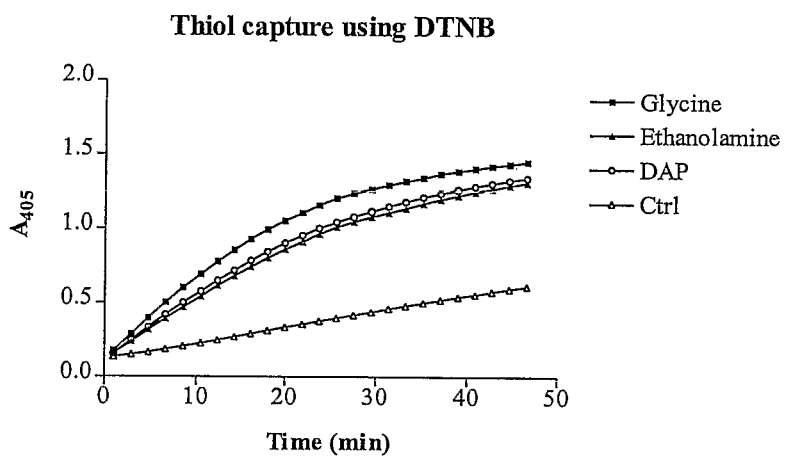
FIG 14 (Example 18)

PRODUCTION OF CONJUGATES

RELATED APPLICATIONS

This application is a U.S. National Phase Application of International Application No. PCT/GB2006/004633, filed Dec. 12, 2006, which claims the benefit of GB Applications 0525223.4, filed Dec. 12, 2005, and 0614533.8, filed Jul. 21, 2006, all of which are incorporated herein in their entirety.

FIELD OF THE INVENTION

This invention relates to the production of conjugates and concerns a method and a kit for performing the method.

BACKGROUND TO THE INVENTION

Conjugates are widely used in bioscience research, diagnostics and medicine. In the simplest case conjugates take the form of a first chemical entity (A), typically a molecule such as a biomolecule, that is linked to a second chemical entity (B), such as a label molecule, to form an AB hybrid. Oligomeric forms, represented by the formula $A_jB_k$, where j and k are integers, are also possible. Conjugates are usually designed for a specific purpose and often involve novel combinations of materials that are not naturally occurring. Typically, one component of the conjugate has the capacity to interact with other molecules (e.g. antigens), e.g. being an antibody, and the second component adds some other useful property (e.g. measurability, ability to kill cancer cells), e.g. being a label.

Conjugates of the present invention may comprise combinations of entities, where A and/or B may comprise one of the following: antibodies, antibody fragments, nucleic acids, beads, polymers, liposomes, carbohydrates, fluorescent proteins and dyes, peptides, radionuclides, toxins, gold particles, streptavidin, biotin, enzymes, chelating agents, haptens, drugs and many other molecules. This list encompasses a vast array of molecules and thus the number of possible combinations in conjugates is almost limitless. It follows that there is considerable scope to create novel hybrid molecules with unusual or unique properties.

One of the most important applications of immunoconjugates is in the quantitation and/or detection of antigens, which are often presented on a surface. For example, in western blotting applications the antigen is immobilised on a sheet of nitrocellulose; in an enzyme-linked immunadsorbent assay (ELISA), the antigen is adsorbed on surface of a polystyrene plate; in immunohistochemistry, the antigen is embedded, along with many other proteins, in a thin slice of tissue, which is attached to a glass slide. While these techniques differ fundamentally in the way in which the antigen is presented to the conjugate, the choice of detection methods is essentially the same. There are two main types. With direct detection, the 'primary' antibody (i.e. the antibody that binds to the antigen) is conjugated to a label that can be measured with a suitable measuring device. With indirect detection, the label is introduced via a secondary reagent, which binds to the primary antibody. The secondary reagent most often is an antibody conjugate comprising a secondary antibody conjugated to a label. More complex detection strategies exist but each of these generally is a variation on one of the above two themes.

With indirect methods, one secondary reagent can be used with a range of unlabelled primary antibodies, which is extremely convenient, although the need for more incubation and wash steps than with direct methods is a major disadvantage. There is also potential for unwanted cross-reactivity of the secondary antibody with immobilised antigens. While direct detection methods offer considerable advantages in terms of speed, cost, and data quality, indirect methods currently predominate. The explanation for this fact is that most primary antibodies are available commercially only in an unlabeled form. Moreover, these reagents are expensive and usually cannot be purchased by researchers in quantities that allow cost-effective production of labelled conjugates using current labelling methodologies.

In order to produce a conjugate, a bifunctional reagent that contains two reactive groups is generally used to link the two components of interest. The reactive groups on the bifunctional reagent are either identical in functionality ('homobifunctional') or different in functionality ('heterobifunctional'). The best-known example of a homobifunctional reagent is the bis-aldehyde glutaraldehyde, which reacts with amines (or hydrazides). Since most biomolecules contain multiple amines, the use of glutaraldehyde commonly results in the formation of high molecular weight conjugates. Furthermore, the polymeric nature of solutions of glutaraldehyde, which can vary considerably with age, means that conjugates prepared with glutaraldehyde are generally quite difficult to reproduce.

Heterobifunctional reagents are generally preferred in the preparation of conjugates as they allow the operator to exert a higher degree of control over the conjugation process. A popular heterobifunctional conjugation strategy involves the coupling of an amine group on one molecule (B) to a free sulfhydryl group (SH) on another molecule (A) via a heterobifunctional reagent (X-Y) having an amine-reactive moiety (X) and a sulfhydryl-reactive moiety (Y). A 'spacer' often separates the reactive moieties of the heterobifunctional reagent; there are many heterobifunctional reagents that have varying spacer structures but which share essentially the same chemical reactivity.

Typically, one biomolecule (B) to be conjugated is reacted via its amine groups with the X functionality of the heterobifunctional reagent, resulting in a B-Y derivative. Excess heterobifunctional reagent is then removed and purified B-Y is reacted with sulfhydryl groups on the other molecule (A). X is commonly an N-hydroxysuccinimide (NHS) ester, while Y may be one of several moieties. Y may or may not be integrated into the final AB conjugate. The sulfhydryl group derived from A is almost always incorporated either as a stable thioether bond or as one half of a reversible (reducible) disulphide bridge between A and B. Y may be any sulfhydryl-reactive functionality including: maleimide, epoxide, iodoacetyl, bromoacetyl, pyridyldithiol, methanethiosulfonate, and the like.

Examples of amine and sulfhydryl reactive heterobifunctional reagents include: N-succinimidyl 3-(2 pyridyldithio) propionate (SPDP); variants of SPDP with extended spacers (LC-SPDP; LC='long chain') and sulfo groups to increase aqueous solubility (sulfo-LC-SPDP); succinimidyloxycarbonyl-α-methyl-α-(2-pyridyldithio)toluene (SMPT); sulfo-LC-SMPT; Succinimidyl-4-(N-maleimidomethyl)cyclohexane-1-carboxylate (SMCC); sulfo-SMCC; m-Maleimidobenzoyl-N-hydroxysuccinimide ester (MBS); sulfo-MBS; N-Succinimidyl(4-iodoacetyl)aminobenzoate (SIAB); sulfo-SIAB; Succinimidyl-4-(p-maleimidophenyl) butyrate (SMBP); sulfo-SMBP; N-(γ-Maleimidobutyryloxy) succinimide ester (GMBS); sulfo-GMBS; Succinimidyl-6-((iodoacetyl)amino)hexanoate (SIAX); and its extended spacer form SIAXX; Succinimidyl 4-(((iodoacetyl)amino) methyl)cyclohexane-1-carboxylate (SIAC); and its extended spacer form (SIACX); p-Nitrophenyl iodoacetate (NPIA).

There are many other related examples, such as the carbonyl and sulfhydryl-reactive linker, β-maleimidopropionic acid hydrazide (BMPH).

The sulfhydryl groups on A may be indigenous. However, more commonly sulfhydryl groups are not present and need to be introduced by a thiolation reaction prior to the conjugation step. In the case of antibodies, thiol groups may be generated by means of a reducing agent (e.g. MEA or dithiothreitol (DTT)), which break disulfide bridges at various positions on the antibody molecule. Alternatively, techniques are known by which other functional groups (commonly amines) can be modified to introduce either a free sulfhydryl group or a protected sulfhydryl group, which can then be deprotected by treatment with a reducing agent to generate a thiolated product (i.e. A-SH). In the known conventional techniques, prior to conjugation with B-Y at least one separation step is required to separate the desired thiolated product A-SH from unreacted thiolation reagent, and any by-products including free sulfhydryl groups that would compete for conjugation to B-Y and possibly also reducing agent that would otherwise compete with A-SH for conjugation to B-Y. Separation is performed by techniques including desalting on chromatography columns, gel filtration, dialysis, or washing. The separation step or steps inevitably result in losses and dilution of material. Because of the tedious nature of the separating step(s) and/or requirement for significant quantities of A, the thiolation step may never be thoroughly optimised.

By way of example, 2-iminothiolane (2IT), which is also known as Traut's reagent (Traut et al., Biochemistry 12, 3266-3273, 1973) has previously been used to introduce SH groups into proteins, particularly antibodies. The reagent reacts with primary amines (e.g. present on lysine) and generates a terminal sulfhydryl group in a ring-opening reaction. Excess Traut's reagent is removed, typically by desalting, prior to conjugation of the resulting thiolated molecule with a thiol-reactive group on another molecule. Although not mentioned in otherwise comprehensive works on bioconjugation chemistry (e.g. Bioconjugate Techniques; G. T Hermanson, Academic Press 1996), 2IT also undergoes a secondary reaction in which the nascent thiol reacts intramolecularly to form an unreactive thioester (Bartlett & Busch., Biol. Mass Spectrom. 23, 353-356, 1994; Singh et al. Anal. Biochem. 236, 114-125, 1996). It is clear from the known chemistry of Traut's reagent that the duration of the thiolation reaction may be critical to the success of the subsequent conjugation step, and that desalting or other separation steps need to be completed quickly.

Conventional prior uses of 2IT in the production of conjugates with molecules engineered to contain thiol-reactive functions employ excess 2IT followed by a desalting, dialysis or wash step. This type of approach is recommended by suppliers of 2IT (e.g. Pierce technical bulletin 0414; product 26101) and of products used in the preparation of bioconjugates (e.g. Prozyme TechNote #TNPJ300). Other publications that describe this approach include: U.S. Pat. Nos. 6,962,703, 6,936,701, 6,669,938, 6,010,902, 5,869,045, 5,164,311; Stanisic et al., Infection and Immunity 71, 5700-5713, 2003; Mandler et al., Journal of the National Cancer Institute, 92, 1573-1581, 2000; Huwyler et al., Proc Natl Acad Sci 93, 14164-14169, 1996.

One potentially promising solution to the problem of desalting was suggested (Haughland. Handbook of Fluorescent Probes and Research Chemicals, 6$^{th}$ edition, Molecular Probes, p 49) which involved reduction of protected sulfhydryl groups by TCEP (Tris(2-carboxyethyl)phosphine). While it is claimed that removal of TCEP is unnecessary, as it does not interfere with subsequent conjugation steps, Getz et al (Anal Biochem 273, 73-80, 1999) showed significant interference of TCEP in conjugation reactions. Moreover, Shafer et al (Anal Biochem 282, 161-164, 2000) reported that TCEP combines rapidly with the sulfhydryl-reactive maleimide and iodoacetyl groups. Furthermore, bioconjugation reactions commonly are carried out in phosphate buffers at pH 7-8, under which conditions TCEP is unstable (Han & Han, Anal Biochem 220, 5-10, 1994). TCEP is very stable at extremes of pH (e.g. in 10 mM HCl or in 100 mM NaOH), which are not compatible with most biomolecules. While TCEP has found certain niche applications its serious limitations have ensured that the preferred methods for producing bioconjugates have changed little since it became commercially available in 1992. TCEP does not contain a sulphur atom and therefore, for present purposes, is not considered a "thiol generator".

McCall et al (1990 Bioconjugate Chem. 1, 222-226) disclosed a one step method for conjugating macrocyclic chelators to antibodies using 2IT. Specifically they used 2IT to join 6-[p(bromoacetamido)benzyl]-1,4,8,11-tetraazacyclotetradecane-N,N$^1$,N$^{11}$,N$^{111}$-tetracetic acid, abbreviated as BAT, or a similar compound, 2-[p(bromoacetamido)benzyl]-1,4,7,10-tetraazacyclododecane-N,N$^1$N$^{11}$,N$^{111}$-tetra acetic acid (abbreviated as BAD), to a mouse antibody. The BAT/BAD reagents were monovalent with respect to sulfhydryl reactive groups i.e. having only one group per molecule able to react with a sulfhydryl group. McCall et al suggested that the "one step" method disclosed therein was applicable only to the particular BAT/BAD reagent ("since under mildly alkaline conditions bromoacetamide reagents react rapidly with sulfhydryl groups but only slowly with amino groups, the antibody, BAT and 2 IT solutions could be combined in a single reaction mixture"). There is no suggestion that this technique might be generally applicable and the standard method used commercially remains a 2 step approach with an intervening desalting, purification or washing stage.

SUMMARY OF THE INVENTION

In one aspect the present invention provides a method of reacting a first chemical entity and a second chemical entity to form a conjugate in which the first and second chemical entities are covalently bound with respect to each other, comprising bringing into simultaneous contact the first chemical entity, the second chemical entity and a thiol generator, wherein the thiol generator reacts with the first chemical entity in a thiolation reaction resulting in formation of a free sulfhydryl group on the first chemical entity, and the free sulfhydryl group reacts with the second chemical entity to form the conjugate, and wherein the second chemical entity is polyvalent with respect to its reactivity with sulfhydryl groups (i.e. one molecule of the second chemical entity can react with two or more sulfhydryl groups).

The present invention differs from conventional prior art techniques in that no separation step is involved between reaction of the thiol generator and first chemical entity and reaction with the second chemical entity. Instead, in the present invention, the three materials are in simultaneous contact at some stage in the conjugation procedure, with the thiol generator acting to produce free sulfhydryl groups on the first chemical entity while in contact with both entities to be conjugated. There is no separation or partial separation of the thiolated first chemical entity from excess thiol generator or from any by-products that might be formed prior to contact with the second chemical entity. An advantage of this approach is that the newly formed, though labile, SH groups can react immediately with the second chemical entity.

The invention is based in part on the realisation that a separation step is not necessary, and that the consistent use of separation in the prior art is based on a misconception. By eliminating the separation step(s) of prior conjugation procedures, the method of the invention is substantially simplified. Further, because there is no separation step with inevitable loss of material, the conjugation reaction of the invention can be performed using very small amounts of materials. The invention thus paves the way for easy formation of conjugates in the form of labelled reagents useful in direct assays, e.g. facilitating direct labelling of almost any protein, on any scale, and offers further benefits of immunoassay simplification, greater reproducibility and cost reduction.

The thiol generator (TG) contains one or more sulphur atoms and reacts with the first chemical entity (e.g. by ring opening, rearrangement or otherwise) to produce a covalently bound sulfhydryl (or thiol) group on the first chemical entity, the sulfhydryl group including a sulphur atom from the thiol generator. The thiol generator conveniently comprises a thiolactone (see below) and/or an iminothiolactone (see below) and/or an episulfide such as 1,2-epithiopropane and/or a thiazolidine such as 2-[(4-dimethylamino)phenyl]-1,3-thiazolidine and N-substituted analogues of thiazolidines, where the said N-substituents may be introduced to modify the ring-opening properties (Canie et al., Pure & Appl. Chem. 68, 813-818, 1996). A mixture of materials may be used. Suitable thiolactones include N-acetylhomocysteinethiolactone (NAHCT) (Benesch & Benesch. Proc. Natl. Acad. Sci. 44, 848-853, 1958). Suitable iminothiolactones include 2-iminothiolane (2IT), also known as Traut's reagent, which is commercially available as 2-iminothiolane hydrochloride. Substituted and derivatised materials may also be used, e.g. 5- and 4,5-alkyl substituted 2-iminothiolane (Goff and Carroll. Bioconjugate Chem. 1, 381-386, 1990). Possible variants include 5-methyl-; 5-tert-butyl-; 5-phenyl-; 5,5-dimethyl-; 5-spiro-; and 4,5-ring analogues.

The first chemical entity (A) includes a chemical functionality that reacts with the thiol generator to produce a thiolated version of A, A-SH. The functionality is generally a nucleophilic group, typically an amine, particularly a primary amine, or a hydroxyl group. Typical thiolation reactions are as follows:

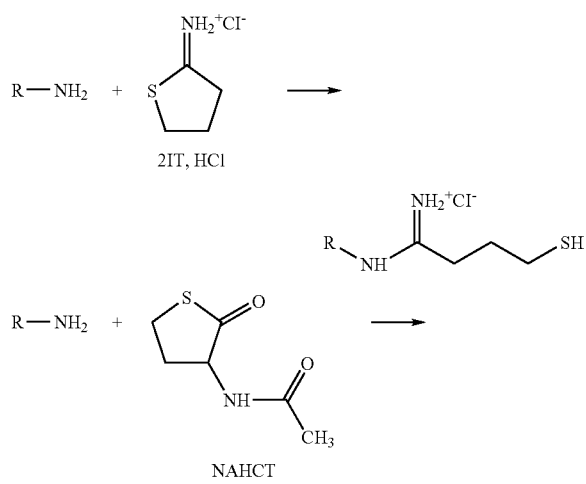

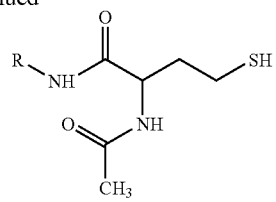

2IT is fully water-soluble and reacts with primary amines in the pH range 7 to 10. In conventional conjugate formation reactions, 2IT is used at a pH of about 8, under which conditions 2IT reacts efficiently and rapidly with primary amines, e.g. in lysine residues present in peptides, polypeptides and proteins. For reaction with primary amines, it has now been found that it is preferable to react 2IT at a pH lower than the conventional value of 8. Thus when using 2IT the conjugation reaction is preferably carried out at a pH less than 8, preferably less than 7.8 and more preferably less than pH 7.7. A preferred pH range is 7.0-7.5. Since the reactions of thiols with many types of thiol-reactive groups Y take place efficiently between pH 6.5 and 7.5, it is undesirable to use TG at high pH values where competing hydrolysis reactions generate undesirable free thiols. Moreover, Y may also be subject to hydrolysis reactions at alkaline pH, as discussed below, or may show reduced selectivity for thiols, as in the case of the popular maleimide functional group. At higher pH, e.g. about 10, 2IT is also reactive with aliphatic and aromatic hydroxyl groups, although the rate of reaction with these groups is only about 0.01 that of primary amines (Alagon & King. Biochemistry 19, 4341-4345, 1980). In the absence of amines, carbohydrates such as agarose or cellulose membranes can be modified with 2IT to contain sulfhydryl residues. Polysaccharides modified in this manner are effective in covalently cross-linking antibodies for use in immunoassay procedures.

The first chemical entity (generally referred to herein as "A") is typically a polymer, preferably a biomolecular polymer (i.e. a polymeric molecule which occurs naturally in one or more living systems). A preferred biomolecular polymer is a polypeptide. Desirably, but not essentially, the first chemical entity comprises or consists of an antibody or an antigen-binding fragment, such as Fab, Fv, scFv or a single domain antibody, or a multimer of an antibody or antigen-binding fragment thereof. Other examples of A include Streptavidin, neutravidin, protein A, polypeptide receptor molecules, and polypeptide ligands. A first chemical entity comprising one or more thiol groups may be represented as A-SH.

Where the first chemical entity includes more than one chemical functionality that reacts with TG, e.g. several primary amines, more than one sulfhydryl group will be formed on the first chemical entity.

The second chemical entity (generally referred to herein as "B") includes a plurality of sulfhydryl-reactive functional groups (Y) that react with the sulfhydryl group formed on the first chemical entity, resulting in production of the conjugate. The second chemical entity may thus typically be represented as B-Y. During the conjugation reaction the sulphur atom of A-SH is usually integrated into the final conjugate as a stable thioether bond or one half of a reversible (reducible) disulphide bridge.

The second chemical entity includes more than one sulfhydryl-reactive functional group which may have identical or different chemistries. Sulfhydryl-reactive entities include maleimide, epoxide, iodoacetyl, bromoacetyl, pyridylolthiol, etc. The plurality of sulfhydryl-reactive functional groups (Y) may be naturally present in the second chemical entity, but commonly it will be necessary for one or more of the sulfhydryl-reactive functional groups to be introduced to a molecule B in a preliminary step to produce the second chemical entity. Suitable introduction techniques are well known to those skilled in the art.

The second chemical entity (B-Y) typically comprises or includes a label e.g. enzyme, fluorescent material etc. for identification or measurement of materials via binding of the conjugated first chemical entity, or a toxin, therapeutic agent etc. for targeted delivery via binding of the conjugated first chemical entity.

The present invention provides a method which is generally applicable. Nevertheless, in preferred embodiments, the second chemical entity is or comprises a polymer. In preferred embodiments the second chemical entity comprises a polypeptide.

In a preferred embodiment the second chemical entity comprises an enzyme. Examples of preferred enzymes include HRP, alkaline phosphatase and glucose oxidase. HRP is especially preferred.

The functions of the first and second chemical entities may be reversed.

Since thiols that do not originate from reaction between A and TG can compete with A-SH molecules for the limited number of Y functions on B, there are certain constraints on the range of conjugation conditions that can be employed. The initial purity of reagents, especially of TG, is an important consideration as this is a potential source of unwanted free thiols (e.g. hydrolysis products of TG). Increasing the pH of the conjugation reaction will tend to deprotonate amines on A, resulting in a faster reaction of amines with TG, but the rate of hydrolysis of TG may increase too. The efficiency of conjugation will therefore depend, as with any chemical reaction, on the concentrations of reactants, but also on the initial level of thiol contamination, the rate of production of A-SH (from a reaction of A with TG) compared with that of other thiols, the relative reactivity of the different thiol-containing molecules with B-Y, and the total amount of Y functions available for conjugation.

The inventor has discovered that conjugations of molecules of the formula $B-Y_n$ (where 'n' is an integer) with A-SH will become more susceptible, to interference from contaminating thiols as 'n' becomes smaller. If n=1, the reaction of a molecule of B-Y with just one molecule of contaminating free thiol will prevent that particular B-Y molecule from participating in any other coupling reactions. Thus, if 'n' is small, a large excess of B-Y may be required to ensure that each A-SH molecule can react with B-Y. The use of excess B-Y may be impractical and uneconomic, particularly if B is a large biomolecule. Moreover, high levels of free B in the final conjugate may be troublesome in certain applications. Instead the inventor realised that an improved method of preparing conjugates in the face of undesirable competing reactions with unwanted thiols was to increase efficiency of the conjugation between A-SH and $B-Y_n$ by using B-Y reagents with high values of 'n'.

The method of the present invention becomes increasingly robust as the value of 'n' increases. Preferably the second chemical entity comprises more than three sulfhydryl-reactive groups per molecule. More preferably the second chemical entity comprises five or more sulfhydryl-reactive groups per molecule. Most preferably the second chemical entity comprises ten or more sulfhydryl-reactive groups. Advantageously the second chemical entity comprises from ten to fifteen sulfhydryl-reactive groups. If the desired number of sulfhydryl-reactive groups are not naturally inherent in the second chemical entity, they may be introduced by chemical or enzymatic synthesis, as described elsewhere. For present purposes, a "sulfhydryl-reactive group" is one which will react with a sulfhydryl group under the conjugation reaction conditions. Clearly the reaction conditions must be such as to substantially preserve the activity of the first and second chemical entities.

In the case of HRP, which has only six lysine residues, only two of which can be exploited for the introduction of Y functions (Bioconjugate Techniques 1996, G T Hermanson, p 632), it is particularly important that reagents have low thiol content and that the reaction conditions do not lead to excessive hydrolysis of TG. However, irrespective of the conditions used, any reduction in conjugation efficiency arising from the production of unwanted free thiols may be countered by introducing more Y groups into B or by polymerising B-Y, or by a combination of these two approaches. The method used to introduce extra Y groups into B is not particularly limited, though the method should preferably substantially preserve the biological activity of B, particularly if B is an enzyme.

An advantage of the present invention is that it avoids the need to employ large molar ratios of second chemical entity to thiol generator (i.e. B:TG ratio) to overcome the presence of interfering free thiols. Thus, in the present invention, the molar ratio of second chemical entity to thiol generator in the conjugation reaction is conveniently not more than 2.0:1, typically 1:1 or less, preferably in the range 1:1 to 1:20, most preferably in the range 1:10 to 1:15.

Y groups can be directly attached to functional groups that are already present on B. Alternatively, or in addition, new reactive centres may be introduced. For example, molecules with sugar chains may be oxidised with sodium periodate to generate aldehyde functions. These functions readily react with amine- or hydrazide-containing compounds to form Schiff bases or hydrazone linkages, respectively, which can be stabilised with sodium cyanoborohydride, sodium borohydride or another suitable reducing agent. Thus if an excess of a diamine compound is reacted with aldehyde groups, one amine moiety will be introduced for each aldehyde that is modified. If the diamine is not present in excess cross-linking reactions (i.e. to give B polymer) may occur, which may be useful in certain situations (see below).

The introduction of amine groups into B is not limited to the reaction of B with simple diamines. Other molecules with two (or more) functional groups may be employed. One of these functional groups must be able to react with B and it must be possible to convert the other functional group into a Y group. Y groups may also be introduced directly into B without utilizing any amine moieties on B. For example, if B is a glycoprotein, reaction with periodate generates aldehyde functions which may subsequently be reacted with a heterobifunctional reagent that has both aldehyde and sulfhydryl reactive groups (e.g. 4-(4-N-Maleimidophenyl) butyric acid hydrazide; MPBH) (Chamow S M et al J. Biol. Chem. 1992 267, 15916-22). Compounds analogous to MPBH (e.g. $M_2C_2H$) may also be used (Bioconjugate Techniques 1996, G T Hermanson, p 250).

Another method of introducing functional groups is to modify carboxylic acids (e.g. as provided by glutamate or aspartate residues in polypeptide chains). Carbodiimide-mediated condensation of amine-containing molecules with carboxylic acids is widely employed in chemical synthesis and can be used to introduce amines (e.g. by reaction with diamines, triamines) and other functional groups into B. For example, aminated HRP has been generated using carbodiimide (EDC)-mediated condensation of HRP with ethylenediamine (U.S. Pat. No. 5,039,607), which gave HRP molecules with 11 amine functions. The carbodiimide approach is particularly useful if periodate-based methods cannot be employed through lack of sugar chains on B.

One advantage of introducing amines into B followed by subsequent conversion into Y functions is that a wide range of potentially useful amine-containing molecules is commercially available. In these molecules, the amine groups may or may not be attached to the same atom. By increasing on B the number of amines (which may ultimately converted into Y groups), derivatives of HRP that are more resistant to thiol interference in conjugation reactions may be generated.

In a preferred embodiment, periodate-activated HRP is reacted with a molecule C which bears 'c' amine groups (where c=2 or more), providing HRP analogues with c−1 additional amines for each aldehyde group modified. In preferred embodiment C is a diamine (e.g. ethylene diamine, propane diamine, butane diamine; 2,2'(ethylenedioxy)bis-ethylamine (EDBA); lysine and the like) or molecules with three or more amine functions (e.g. lys-lys (c=3), trilysine (c=4), Jeffamine T403 (c=3), aminated dextrans, aminated dendrimers and other polyamino species.

An alternative strategy to reduce the impact on conjugation efficiency of unwanted free thiols is to induce polymerisation of B-Y, which provides a polymer [(B)n]q with nq maleimide functions, where 'n' is the number of Y functions per molecule of B in the polymer, and 'q' is the average number of B molecules in a polymer. Thus even in situations where 'n' is small, the impact of free thiols is reduced because the B molecules are physically connected and conjugation of A-SH to any one of the available Y functions effectively tethers all B molecules in the polymer to A. Another advantage of this approach is that the sensitivity of detection might be increased as a larger number of, for example, HRP molecules potentially can be attached to A. The use of polymeric HRP in immunoassays to increase assay sensitivity is well known and such forms are commercially available.

Alternatively, B molecules (rather than B-Y) with free amines (either occurring naturally or introduced for example by reaction with diamines) may first be polymerised by reaction with homobifunctional crosslinking agents (e.g. dialdehydes) or by use of heterobifunctional reagents to promote coupling of amines to other functional groups on B. Heteropolymers may also be generated by reaction of B with 'scaffold' molecules (e.g. dendrimers, dextrans, proteins) to which multiple B molecules may be appended. This may involve reactions of amines on B with aldehydes on the scaffold or with other available functional groups (e.g. thiols) mediated by heterobifunctional crosslinking reagents. In turn, remaining unreacted surface amine functions can be converted into Y groups by reaction with a heterobifunctional reagent such as SMCC. If insufficient free amines remain after the polymerization step, further amines can be appended prior to introduction of Y groups. For example, if carbodiimide chemistry is used to introduce amines into B which are then utilized, or partly utilized, in polymerization reactions, a different chemistry (e.g. periodate activation of sugar chains) may be used to introduce additional amines (which can then be converted into Y groups) or to introduce Y groups directly (e.g. by reaction with MPBH). Polymerised HRP may also be obtained from commercial sources and further modified to create multiple Y functions for use in the present invention.

B molecules that confer useful properties on conjugates are often prepared and stored in B-Y form for later use. For example, some labels are available commercially as maleimide-activated derivatives (lyophilised maleimide-activated enzymes, or maleimide or iodoacetyl derivatives of small fluorescent molecules). B-Y may also be freshly prepared if required using methods known in the art. Examples of B include enzymes such as horseradish peroxidase (HRP), alkaline phosphatase, and glucose oxidase (Gox); fluorescent molecules such as phycobiliproteins (e.g. allophycocyanin, phycoerythrin), low molecular weight dyes (e.g. fluorescein, rhodamine) and the like. Bridging or linker molecules include streptavidin or biotin. Cell killing agents include toxins (e.g. ricin, and radioisotopes). The enzymes HRP and alkaline phosphatase are especially widely-used enzyme labels for antibodies and other polypeptides, and these enzymes represent preferred examples of the second chemical entity.

When practising the invention A, TG and B-Y are combined and incubated for suitable period of time. The order of addition may be varied to suit circumstances.

For example, in one approach in a first step TG is mixed with A. After a suitable period of time during which A-SH is generated, in a second step the mixture is added to B-Y. A suitable period of time is any time that affords an efficient conjugation between A and B-Y. The period is typically up to 18 hours (i.e. overnight), but may be performed within about 2-4 hrs under optimum conditions. The reaction conditions in the two reaction steps may be varied if appropriate, for example the first and second steps may be carried out at different pH values by use of appropriate buffers.

In another approach, A is mixed with B-Y after which the mixture is contacted with TG.

In a further approach, TG is mixed with B-Y and the mixture is then contacted with A.

Desirably, either one or both of TG and B-Y are initially in dried condition e.g. being freeze-dried or lyophilised for storage stability. Preferably, a solution (typically aqueous) of the first entity is used to reconstitute the other components, which leads to minimal expansion of the sample volume.

In a particularly preferred embodiment, A is added in liquid form to a lyophilised mixture comprising both B-Y and TG.

Alternatively, a lyophilised mixture of TG and B-Y is reconstituted with a solvent (typically water) to give a mixture not containing A, to which A is subsequently added.

The solution in which the conjugation reaction takes place may optionally include one or more components in addition to A, B-Y and TG. These components may or may not affect the rate of the conjugation reaction. For example, some additives might be introduced prior to lyophilisation of components, primarily for the purpose of stabilising said components or for ease of dissolution. Other components, especially buffers, may be employed primarily to provide conditions of pH under which the preferred reactions take place at a suitable rate. These buffers may be introduced into the final conjugation mixture via one or more additions such that the final mixture has the required composition. Preferably, though not obligatorily, the buffering substances are included along with one or more of the other components (A, B-Y or TG, or a combination thereof), to minimise the amount of labour in preparing the conjugate.

The stability of TG and the conditions required to effect conjugation should be carefully considered when determining the preferred order of adding components to the reaction mixture. For example, base labile TG might be stored in acidic medium (or lyophilised from such medium) and introduced last into a suitably buffered reaction mixture. The buffered mixture can be designed to accommodate the acid introduced along with TG and provide a final pH and composition that is suitable for the intended conjugation reaction to take place.

Suitable conditions of, for example, temperature, pH and concentration for the conjugation reaction will depend upon the nature of the reagents. Suitable conditions can readily be determined by those skilled in the art by means of routine trial and error.

The method of the present invention also provides the basis of a conjugation kit. TG and B-Y are provided preferably as dried, e.g. freeze-dried (lyophilised) components, either separately or as a mixture, in suitable vessels, along optionally with a suitable buffer in which A can be dissolved. Alternatively, A can be desalted or dialysed into the said buffer, particularly if the formulation of A contains components that might interfere with the conjugation reaction.

In a further aspect the invention thus provides a conjugation kit for use in the method of the invention, comprising at least one sample of reagent selected from a first chemical entity, a second chemical entity and a thiol generator, and instructions for performing the method of the invention.

The kit desirably comprises samples of at least two reagents selected from a first chemical entity, a second chemical entity and a thiol generator.

The kit preferably comprises a sample of a second chemical entity and a sample of a thiol generator. These two reagents may be provided separately or may be in the form of a mixture. The thiol generator is preferably present in excess in relation to the second chemical entity, e.g. up to about 20 times molar excess.

A plurality of aliquots or samples of reagents or reagent mixtures are preferably provided in suitable containers, e.g. in individual tubes, vials or in the wells of a multi-well (e.g. 96 well) microtitre plate. Samples may be provided in a range of different predetermined amounts, so a user can select the appropriate sample size having regard to the material (e.g. first component) to be treated. One preferred embodiment comprises a plurality of samples of mixtures of second chemical entity and thiol generator in a range of different amounts for use in conjugating one or more a different first chemical entities (possibly supplied by an end user) e.g. for labelling a range of different molecules, for instance antibodies to be used in direct immunoassays.

The samples of reagent or reagent mixtures may optionally include other materials such as buffers etc. to provide appropriate conditions for reaction.

Where the thiol generator comprises 2IT, the samples of 2IT are preferably at a pH below 8, more preferably below 7.8 and yet more preferably below 7.7. A preferred range of pH is 7.0-7.5.

The kit may include optional ingredients such as solvent, buffer solutions etc.

The reagent samples are desirably in dried, e.g. freeze dried (lyophilised) form for storage stability. Desirably the reagent samples are freeze dried from an aqueous solution comprising sodium phosphate buffer at a pH in the range 5-6.5, preferably 5.0-6.0. Desirably also the reagent samples are freeze dried from an aqueous solution comprising $Mg^{2+}$ ions, especially at a concentration in the range 1-10 mM $Mg^{2+}$. Conventional cryoprotectants and lyoprotectants may also be present, such as polyols, especially trehalose or dextran.

In a preferred embodiment, lyophilised reagents are provided in small polypropylene tubes (e.g. 0.5 ml or 1.5 ml Eppendorf tubes), polypropylene cryovials or vials, glass vials, 96-well polypropylene or polystyrene microplates, and other receptacles appropriately sized for the intended conjugation reaction. Preferably, the material of the vessel does not significantly react with TG to release thiol groups either before lyophilisation or upon subsequent reconstitution with a suitable solvent. The nature of the vessel is not particularly limited to the aforementioned examples.

Suitable buffering components for use in the present invention include phosphate buffers, especially sodium phosphate, N-(2-Hydroxyethyl)piperazine-N'-(2-ethanesulfonic acid) (HEPES), 2-morpholinoethanesulfonic acid (MES), 3-(N-morpholino)propanesulfonic acid (MOPS), bicarbonate and other buffers that do not react with TG, or react relatively slowly when compared with the rate of reaction of TG with functional groups on A. The list may therefore contain amine-containing buffers that react at a suitably slow rate.

Other components of the conjugation reaction mix may include salts (e.g. NaCl) and other inorganic or organic components that do not directly participate in the reactions but provide a suitable environment that stabilises components or in some other way facilitate the desired reactions or minimise losses, for example, on the surfaces of vessels.

Since TG is reactive it may react with other nucleophiles in the conjugation mixture. Water is a weak nucleophile but it is present at a high concentration and hydrolysis reactions could increase the concentration of thiols not covalently associated with A, especially at pH values significantly above pH 7.

Preferably the TG includes little or no free thiol groups, with the level suitably being below 5% in molar terms, preferably below 3% in molar terms and more preferably below 1% in molar terms.

TG from commercial sources may contain significant quantities of free thiol, and free thiols may also be generated over a period of time in storage. Free thiols could compete with A-SH for Y groups on B-Y and reduce conjugation efficiency. In the case of 2-iminothiolane, one supplier states that contamination with free thiols is 'up to 5%'. The batches used for work described here were measured at about 1% thiol content in molar terms.

It is preferred that the molar ratios of the reactants are carefully selected so that small quantities of free thiols possibly present in TG do not impact significantly on conjugation efficiency. Traut's reagent is more stable than other molecules that are used to introduce thiols or protected thiols and it is not necessary to use large molar excess. Some amine-reactive heterobifunctional reagents with NHS groups have short half-lives in aqueous solutions and are used in large excess to compensate for rapid hydrolysis. Typically, TG is used in reasonable excess, e.g. 10 times molar excess over relevant chemical functionality such as amines present on the first chemical entity to be sure that all molecules of the first chemical entity are thiolated. However, in selecting a suitable concentration of TG the user must have regard for the likely rate of reaction, which is influenced by the pH of the solution. A suitable concentration of TG at a fixed pH is readily determined by examining the effect of varying the concentration of TG on the performance of the resulting conjugates. It is preferred that the reaction conditions allow efficient thiolation of A, but that excessive thiolation is avoided so as not to damage the biological activity of A. Equally, excessive amounts of the second chemical entity should not be conjugated to A-SH otherwise this might lead to suboptimal performance of the conjugate. The second chemical entity is typically present in modest excess, e.g. up to about 5 times molar excess, in relation to the thiolated first chemical entity, to be sure all of the first chemical entities are conjugated. After reaction, excess materials can be removed by any suitable techniques.

Using methods taught in the present invention a conjugation reaction might contain just 10 μg of an IgG antibody (Mr 150,000). Typically about 5 thiol groups per molecule are introduced. Thus in a 10 μl volume (6.7 μM antibody) the concentration of amines (to be modified) is ~33 μM. Since there is no desalting step, nascent thiols will react immediately with B-Y. For a label such as maleimide-activated HRP (molecular weight 40,000) the labelling of all nascent thiols would require ~33 µM enzyme, which corresponds to ~13 µg of HRP in a 10 µl reaction volume. If a 25-fold molar excess of TG were used, 1% thiol contamination in the solution of TG would represent a concentration of about 8 µM, or ¼ (in molar terms) of the maleimide-activated HRP present. Moreover, if HRP were labelled on average with 2 or more Y groups per molecule, the reaction of an HRP molecule with one contaminating free thiol would not necessarily prevent that molecule from conjugating with B-Y. It follows from this that the use of excess B-Y, or B-Y with multiple Y groups, might ameliorate the negative effects of contaminating free thiols and those generated by hydrolysis of TG during the conjugation reaction. In some applications, especially those with antigen immobilised on a surface, the use of excess B-Y is not problematic as the surplus reagent (i.e. not linked to A) can simply be washed away during the immunoassay. Moreover, it is common to use excess B-Y to minimise the amount of unreacted A-SH, which would compete with AB and reduce assay sensitivity.

In some immunoassay applications, especially those in which the antigen is measured in free solution, it may be desirable to maximise the amount of conjugated B and minimise free B-Y. This can be achieved by purification of AB from the conjugation mix using methods known in the art or by careful control of the reaction conditions. In the present invention, the avoidance of desalting steps, from which the yield of materials is difficult to determine, especially when there is a need to progress quickly to the conjugation step, greatly assists in establishing precise ratios of the reactants and in optimising the conditions to meet specific experimental objectives.

The level of free thiols becomes more important if the concentration of free B-Y needs to be kept low, since unwanted thiols might render B, and especially B that is lightly decorated with Y (that is, the value of n in B-Y, is low, e.g. at or near 1), incapable of conjugating to A-SH. Where separation of free B-Y following conjugation is difficult or undesirable, it is preferable to minimise side reactions by using conditions (i.e. low pH, amine-free buffers) that do not cause non-A-dependent thiol release.

Free thiols may be removed or largely removed before TG is used for the purpose of thiolating A. For example, free thiols may be removed by purification using a solid support to which TG and the free thiol form show different affinities, thus allowing for the selective elution of relatively pure TG. The binding to the solid support may be covalent or non-covalent.

In one approach a solution of TG is contacted with a solid support to which Y groups have been attached. Such materials are commercially available, as in the form of iodoacetyl Sepharose (Pierce) (Sepharose is a Trade Mark) or can be made using methods known in the art (J. Biol. Chem. 245 3059-3065 (1970) by carbodiimide-mediated conjugation of haloacetates to amine-bearing agarose beads. In a preferred embodiment the number of Y groups exceeds the number of free thiols such that the solid support is able to capture all, or substantially all, of the unwanted free thiols via a covalent bond. The TG not binding to the solid support preferably is used immediately or quickly frozen and lyophilised to preserve the material largely in an intact state.

Another approach is to measure the concentration of free thiol in samples of TG e.g. using the well-known 5,5'-dithiobis(2-nitrobenzoate) (DTNB) method, or other suitable method for measuring free thiols. A solution containing a Y-bearing molecule and lacking functional groups that might interfere with subsequent conjugation steps is then added, preferably in slight molar excess and preferably under conditions in which (a) further thiols are not generated or are generated very slowly (b) the contaminating thiols react quickly with Y to form a stable thioether, thus eliminating thiols from the sample. This strategy can of course be used to remove thiols regardless of their source.

The Y-bearing molecule suitably contacts TG for a period of time that allows most of the free thiol to react with Y. After the said period of time, the TG sample is contacted with A and B-Y. The molecule used to remove free thiols may be one of the following: N-ethylmaleimide, iodoacetamide, iodoacetate, bromoacetamide, bromoacetate, chloroacetate, mercurial compounds and the like. N-ethylmaleimide is particularly preferred.

By contacting A, TG and B-Y at the same time, in accordance with the invention, TG may be afforded the opportunity to react with amines that are present on B-Y, as well as A. If B is a large biomolecule it is quite likely that free amines will still be present, even if Y groups have already been introduced via chemical modification of available amines. In the case of HRP, a very popular label in bioconjugate chemistry, the number of amines per molecule is unusually low (0.15 per kDa), compared with 0.88/kDa for bovine serum albumin (BSA) and 0.44/kDa for ovalbumin. Thus the degree of reaction of TG with B-Y can be controlled by varying (i) the type of B used (ii) the density of Y groups on B (with respect to residual free amines) (iii) the order of addition of reagents.

Where the level of amines on B is high and, under the experimental conditions used, a significant reaction with TG occurs, B might be partially polymerised (i.e. reaction of B-Y with nascent B-SH). Where this is considered undesirable, simply adopting a two-step conjugation strategy will circumvent the problem. First, TG contacts A and after a suitable period of time in which A-SH is generated the mixture is contacted with B-Y. This allows AB conjugates to be formed before significant amounts of B polymer can be generated.

Partial polymerisation of B-Y may be advantageous in some situations. One simple approach to increase immunoassay sensitivity is to attach more B per molecule of A. Polymerisation of B-Y has been used to achieve this goal. By careful selection of reagent concentrations (TG, A) and the duration of the first step (A-SH production) and consideration of the number of free amines and Y groups on B, the extent of in situ B polymer production can be manipulated as required.

While the one-step conjugation method of the present invention is exceptionally attractive, with all reagents combined together in a single step, two-step variants (e.g. involving two reagent addition operations instead of one) are still remarkably simple compared with most present conjugation methods, and have the benefit of providing further options, if required, to optimise conjugates for specific applications.

For example, in one embodiment, a reaction is set up under conditions that favour the production of AB conjugates (from A-SH and B-Y). In a separate reaction, B is reacted with TG to generate a solution containing B-SH, which is then added to pre-formed AB complexes, which may contain unreacted Y groups. By introducing B-SH, a controlled increase in molecular weight of conjugate can be obtained through a coating of B-SH on AB-Y molecules. By careful consideration of the input of B-Y and the density of Y groups, the initial conjugate can be engineered to react to varying extents with molecules of B-SH.

Some applications may require conjugates of relatively low molecular size. Applications that involve penetration of reagents into an antigen-containing sample (e.g. immunohistochemistry) will normally work best with low molecular weight conjugates. However, if the antigen is deposited and exposed on a surface (e.g. nitrocellulose, as in western blotting) it may show greater sensitivity with a higher molecular conjugate. Thus a consideration of the intended use determines the preferred approach for developing the conjugate.

In the preparation of immunoconjugates using thiol-based strategies it is common to employ a 'blocking' step at the end of the conjugation reaction to remove any unused thiols. In some cases this step is not actually required but is performed as a matter of routine. In the present invention there is unlikely to be any need for a blocking step if TG is 2-iminothiolane as the thiols involved in coupling are self-limiting because of the secondary intramolecular reaction. However, since the ring-opening reaction must precede any decay via the secondary intramolecular reaction, or via conventional thiol blocking strategies, a simple deactivation step may be utilised to accelerate ring opening of excess TG.

The quickest method for halting conjugation and deactivating TG is to add a nucleophile (Nu), e.g. glycine, in a suitable buffer. The rate of deactivation is a function of pH and type and concentration of Nu; the conditions employed to deactivate TG must be compatible with the conjugate and preferably the application in which the conjugate will be used, otherwise a purification step will be required. Thiols released from TG in this way will react intramolecularly or with excess Y groups on B-Y or AB-Y. Thus the addition of Nu can deactivate both TG and, indirectly, Y groups. Since the released thiols may form a covalent link to AB the choice of Nu needs to be carefully considered so as not to introduce unwanted groups derived from Nu (e.g. bulky substituents) to the conjugate. However, treatment of the mixture with a low molecular weight thiol (e.g. mercaptoethanol) prior to ring opening of TG may be carried out to deactivate Y groups if required.

The conjugation reactions are conveniently terminated by the addition of Nu e.g. glycine to attack excess TG and also by addition of a thiol-blocking reagent (TBR), such as N-ethylmaleimide, which is commonly employed in bioconjugate chemistry for this specific purpose. However, the combination of glycine as Nu and N-ethylmaleimide as TBR is not meant to be limiting and many other possible Nu materials and thiol blockers will be apparent to one skilled in the art.

In a preferred embodiment Nu and TBR are introduced sequentially. Preferably, Nu is added before TBR. Preferably TBR is added in slight excess over released free thiols. The level of free thiol can be determined, for example, with DTNB. Where the level of thiol cannot be measured, TBR is added in slight excess over the known level of TG, since the level of thiol cannot exceed the initial concentration of TG, if TG is the only source of free thiol.

In one embodiment, the conjugate mixture is simply contacted with Nu (e.g. 50 mM glycine in phosphate buffer or phosphate buffered saline (PBS), pH 8.0). Optionally, the mixture may be further supplemented with thiol blocking reagents (e.g. N-ethyl maleimide), stabilisers (e.g. BSA, ovalbumin or other proteinaceous components; glycerol) and anti-microbial reagents (e.g. sodium azide) or other preservatives. Conjugate may be stored at 4° C., or in small aliquots frozen at −20° C., or in liquid form at −20 (i.e. with 50% glycerol) or frozen at −70° C., depending on the nature of the conjugate and its temperature stability and sensitivity to freeze-thaw.

One area of application of the present invention is in the production of conjugates for immunisation. A significant number of primary antibody reagents are prepared against small peptides, which are usually conjugated to a carrier protein. Suitable carriers include maleimide-activated keyhole limpet haemocyanin (KLH), BSA, ovalbumin, and the like. For peptide antigens that have not been chemically synthesised with terminal cysteine residues, and for other small molecules containing only amines, the present invention allows the generation in situ of thiol functions for coupling to e.g. a maleimide-activated carrier. The avoidance of desalting steps is significant here, not simply because the procedure is more convenient, but also because for molecules of low molecular weight purification following thiolation is often difficult or impossible. In such applications the presence of excess B is not problematic and in molar terms B can greatly exceed A, to ensure that there is excess nascent thiol to couple to all maleimide functions on the carrier.

Another application of bioconjugates is in immunotoxin therapy, which involves antibody-mediated delivery of substances that can kill specific cell types (e.g. cells expressing antigens that are diagnostic of the cancerous state). Some of these toxins are extremely dangerous and represent significant hazard to those engaged in the production of therapeutic agents. The inherent simplicity of the present invention affords the opportunity to conjugate powerful toxins to antibodies without generating dangerous liquid waste from desalting columns or dialysis steps. For example, samples of ricin might be contained in a suitable vessel and the entire conjugation procedure carried out in that same vessel. In this situation, the antibody preferably is maleimide activated and combined with the toxin, which is treated in situ with TG to release thiols for the conjugation reaction.

Another application relates to labelling with B molecules that include fluorescent amine-containing small molecules. Mostly, fluorescent dyes are NHS-activated and are reacted with amines on A. Such reagents are very unstable in aqueous solutions and deteriorate rapidly if not stored in a dry state. Consequently, the preferred approach often is to use excess reagent followed by purification of AB from B. However, an alternative approach is to mix a stable amine-containing fluorophore with a lyophilised maleimide-activated carrier and generate a reactive thiol in situ using TG. In this way excess highly unstable fluorophore is not required and the dye does not contain a reactive group that can be hydrolysed upon storage.

The methods of the present invention teach how conjugates may be made using proven heterobifunctional chemistry but without the troublesome desalting steps that increase labour and limit its application to components that are available in relatively large quantities. Multiple thiolation experiments can be performed using tiny amounts of material and conjugate performance can be optimised rapidly and cost-effectively. The methods described in the present invention lend themselves readily to automation. For example, exploration of 96 different thiolation conditions in a microtitre plate would be considered straightforward using present robot technology. Optimisation of thiolation procedures on this scale would be completely impractical in processes involving desalting or dialysis steps.

One of the major applications of the present invention is labelling of primary antibodies. Since existing antibody reagents may have been formulated without consideration of direct labelling, a number of additives include anti-microbial agents such as sodium azide, and stabilisers such as BSA or glycerol might be present. Furthermore, the antibody storage buffer may not be one of the preferred buffers for conjugation reactions. In other cases, the antibody might be provided as a crude sample of frozen serum or ascites fluid.

For samples that contain additives such as BSA or other proteins derived from animal fluids, including substances from tissue culture processes (e.g. foetal calf serum) the antibody may be a minor component and difficult to label selectively. Fortunately, methods for purifying antibodies are well known, and include biospecific affinity chromatography on a support matrix to which the antigen has been attached. Other suitable methods include support matrices with coupled protein A, protein G, and the like, which can be used to purify IgG from complex mixtures by exploiting interactions with the Fc regions of mammalian IgGs. The elution buffer should be carefully selected to facilitate subsequent conjugation reactions. For example, in affinity chromatography elution is often performed using low pH buffer (e.g. glycine pH 2.3), which would not be suitable, at least not if the material were to be added directly to the conjugation mixture. Other low pH buffers those are more preferable include citrate/citric acid and those based on HCl/NaCl mixtures.

Another approach for removing substances such as BSA is chromatography on a resin such as Blue-Sepharose (Amersham). The advantage of this approach is that the antibody passes through the resin and is not exposed to low pH treatment, which could damage some antibodies. A new product Melon (Melon is a Trade Mark) gel from Pierce has recently been made commercially available, which apparently removes a broad range of proteins from antibody samples. However, subtractive methods such as these do not remove unwanted low molecular weight substances.

Methods that involve purification of the antibody of interest by binding to an antigen or protein on a support matrix have the advantage that all unwanted molecules are washed away. Where low pH elution cannot be used to disrupt the antibody:antigen interaction, perhaps because of risk of damage to one of the components, an alternative elution strategy, such as hypotonic elution (e.g. Gee & Kenny, Biochem J. 230, 753-764, 1985) can be used.

A variety of applications have been exemplified, and show that the invention will allow primary antibodies and other reagents, which are generally expensive and available to researchers in small quantities, to be labelled easily. This is likely to result in far greater use of direct detection methods, which have a number of advantages over other indirect methods of antigen detection.

For the avoidance of doubt it is hereby explicitly stated that any feature described herein as "preferred", "desirable", "convenient", "advantageous" or the like may be employed in the invention in isolation, or in combination with any one or more other features so described, unless the context dictates otherwise.

The invention is further described, by way of illustration, in the following Examples which refer to the accompanying figures in which:

FIG. 1 is a bar chart of absorbancy versus concentration of 2IT showing results of ELISA of Ab1-HRP conjugates as tested in Example 4;

FIG. 2 is a graph of absorbancy versus pH showing the effect of varying pH on conjugation efficiency as tested in Example 5;

FIG. 3 is a graph of absorbancy versus pH showing pH optimum for Ab1-GOX conjugation as tested in Example 6;

FIG. 4 is a bar chart of absorbancy for various different buffers showing the effect of buffer type on conjugation efficiency as tested in Example 7;

FIG. 5 is a pair of graphs of absorbancy versus pH for phosphate buffer and Tris buffer as tested in Example 8;

FIG. 6 is a graph of absorbancy versus time showing the time course of conjugate formation as tested in Example 9;

FIG. 7 is a bar chart of absorbancy for different samples showing the effect of varying the order of addition of reagents as tested in Example 10;

FIG. 8 is a graph of absorbancy (arbitrary units, 405 nm) against conjugate dilution (log scale), showing performance in an ELISA of two different batches of EDBA-HRP-IgG conjugates (solid circles and empty circles) compared with that of an OLA-HRP-IgG conjugate (squares). Control data generated with an antigen-free microtitre plate are superimposed on the baseline.

FIG. 9 is a graph of absorbancy (arbitrary units, 405 nm) against conjugate dilution (log scale) showing the performance in an ELISA of EDBA-HRP-Ig conjugates prepared at pH 6.5 (open circles), pH 7.0 (solid circles), pH 7.5 (squares) or pH 8.0 (triangles).

FIG. 10 is a graph of absorbancy (arbitrary units, 405 nm) against conjugate dilution, (log scale) showing the performance in an ELISA of an EDBA-Gox-Ig conjugate (solid circles) and an OLA-Gox-Ig conjugate (open circles).

FIG. 11 is a graph of absorbancy (arbitrary units, 405 nm) against conjugate dilution (log scale), showing the performance in an ELISA of an iodoacetyl-activated EDBA-HRP-Ig conjugate (data for control superimposed on the baseline).

FIG. 12 is a bar chart of absorbancy (405 mm) against ratio by weight of Ig to mal-EBDA-HRP (solid black bars) or mal-OLA-HRP (shaded grey bars).

FIG. 13 is graph of absorbancy versus time showing the release of thiol from 2IT by various amines as tested in Example 17;

FIG. 14 is a graph similar to FIG. 13 showing thiol capture using DTNB as tested in Example 18.

EXAMPLES

Example 1

Figure 15:
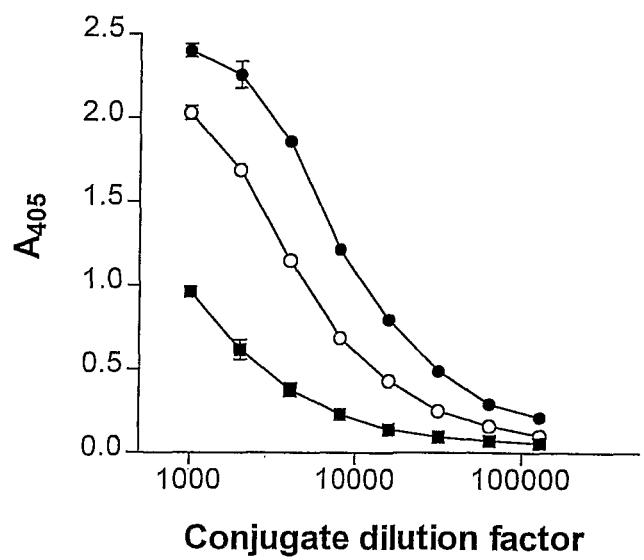
FIG. 15 is a graph of absorbancy (405 nm) against conjugate dilution factor, showing ability of freeze-dried reagents to form conjugate active in ELISA after storage at different temperatures.

HRP (5 mg) (Sigma, P6782) (B) in 0.5 ml of 100 mM sodium phosphate, pH 7.2, was activated with sulfo-SMCC (4 mM) (Pierce, 22322) for 1 hour at 25° C. The maleimide-activated HRP ('mal-HRP') (B-Y) was desalted on a PD10 column (Amersham Biosciences) equilibrated with 10 mM sodium phosphate, 150 mM NaCl, 1 mM ethylenediaminetetraacetic acid (EDTA), pH 7.03. The activated protein (2.5 mg/ml) was used either immediately or lyophilised.

Example 2

Glucose oxidase (5 mg) (Biozyme GO3B3) in 0.5 ml of 100 mM sodium phosphate, pH 7.2, was activated with sulfo-SMCC (2 mM) for 30 min at 25° C. The maleimide-activated Gox (mal-Gox) was desalted and processed as described in Example 1.

Example 3

Rabbit IgG (Sigma I5006) was dissolved at 1 mg/ml in Tris buffered saline (TBS) (50 mM Tris/150 mM NaCl, pH 8.0) and stored in small aliquots at −70° C. To prepare coated ELISA plates, the IgG was thawed and diluted in TBS to 20 µg per ml. Nunc maxisorb plates (clear, 96-well) (code 071832) were incubated with 50 µl (1 µg) of IgG per well. Plates were coated for >1 hour at room temperature and then wrapped in foil and transferred to 4° C. for storage. Coated plates were used within 10 days. Immediately before use, plates were blocked with TBS/0.1% BSA, pH 8.0, for >30 min. To test conjugates by ELISA, duplicate or triplicate wells were incubated with 50 µl of conjugate suitably diluted in TBS/0.1% BSA. After 60 minutes at 25° C., plates were washed five times with TBS. A suitable substrate (see below) was added and absorbance was determined after 2 or 10 minutes at an appropriate wavelength (depending on the label used) using a Victor3 model 1420 multi-label counter (Perkin Elmer). HRP activity was measured using 1 mM 2,2'-azino-bis-(3-ethyl-benzothiazoline-6-sulfonic acid) (ABTS) substrate in 50 mM sodium acetate, pH 5.0, containing 1 µl $H_2O_2$ per ml of reagent. Gox activity was measured in a coupled assay system using 100 mM sodium acetate, 100 mM glucose, pH 5.0, containing HRP (50 µg/ml) and 2 mM ABTS. Alkaline phosphatase activity was measured using 5 mM para-nitrophenyl phosphate (PNPP) in 50 mM glycine buffer, pH 9.6, containing 1 mM $MgCl_2$ and 0.5 mM $ZnSO_4$.

Example 4

Lyophilised anti-rabbit IgG antibody (1 mg) (Sigma R2004) ('Ab1') was resuspended in 1 ml of 150 mM NaCl and stored at 4° C. The following stocks of 2-iminothiolane (2IT) in 1.2 mM HCl were prepared: 100 mM, 100 mM, 10 mM, 1 mM, 0.1 mM and 0.01 mM. Ab1 (A), mal-HRP (B-Y) (prepared as described in Example 1) and buffer (100 mM sodium phosphate, 1 mM EDTA, pH 7.4) were combined in a 1:1:2 ratio and 20 µl portions were dispensed into 1.5 ml Eppendorf tubes. Tubes received 5 µl of 2IT (TG) to give final 2IT concentrations of 200 mM (C7), 20 mM (C8), 2 mM (C9), 0.2 mM (C10), 0.02 mM (C11) and 0.002 mM (C12). A control tube (neg) received 1.2 mM HCl instead of 2IT. 'Pos' is a positive control antibody, diluted 1/1000 (Sigma A6667). After 90 minutes, samples C7-C12 were diluted with TBS/0.1% BSA and tested by ELISA using the procedure of Example 3 at a dilution (with respect to undiluted Ab1) of 1/200. Results are shown in FIG. 1.

As can be seen in FIG. 1 there is a bell-shaped dependence of absorbancy versus 2IT concentration. At low concentrations of 2IT this effect is probably explained by insufficient thiolation of Ab1 to allow efficient conjugation. At high concentrations, the effect is probably explained by damage of Ab1 through excessive modification of lysine groups, though other explanations are possible. For example, commercially available 2IT is contaminated with a small percentage of free thiols, which could compete with thiolated Ab1 for reaction with mal-HRP at high concentrations of 2IT. There is little absorbancy in the absence of 2IT (neg). Absorbancy values for control wells were low (<0.1) except for C7 (~0.25). The data obtained for control wells (with no coated antigen) were subtracted from data obtained for antigen-coated wells to give the values shown in FIG. 1. This experiment shows that it is possible to combine 2IT, Ab1 and mal-HRP in a single tube and generate active conjugates.

Example 5

The effect of varying pH on conjugation efficiency was examined using a series of phosphate buffers prepared by mixing 0.2M $Na_2HPO_4$ and 0.2M $NaH_2PO_4$ in varying proportions: 10:0 (buffer P1, pH 9.29); 9:1 (buffer P2, pH 7.72); 4:1 (buffer P3, pH 7.38); 7:3 (buffer P4, pH 7.14); 3:2 (buffer P5, pH 6.94), 1:1 (buffer P6, pH 6.75) 2:3 (buffer P7, pH 6.58); 3:7 (buffer P8, pH 6.39); 1:4 (buffer P9, pH 6.12); 1:9 (buffer P10, pH 5.81); 0:10 (buffer P11, pH 4.29). Ab1 (prepared as described in Example 4) and mal-HRP (2.5 mg/ml) (from Example 1; lyophilisate reconstituted with water) were mixed 1:1 and 20 µl aliquots were dispensed into Eppendorf tubes. Each tube then received buffer (one from P1-P11) (20 µl) followed by 10 µl of 5 mM TG (i.e. 1 mM final concentration). After 60 minutes, 950 µl of TBS/0.1% BSA, pH 8.0 was added and samples were analysed by ELISA using rabbit IgG-coated plates (see Example 3). The results are shown in FIG. 2.

As can be seen in FIG. 2, active conjugates could be produced under a wide variety of conditions and only at extremes of pH were the reactions rather inefficient. Interestingly, the optimum pH (~7) is substantially below the pH typically used for thiolation of biomolecules with 2IT. A pH of 8.0 or above is commonly currently used, which tends to deprotonate amines and increase the rate of reaction with 2IT. However, for in situ thiolation with 2IT in the presence of a maleimide-activated biomolecule, these conditions are clearly not optimal. This might be explained by increased hydrolysis of maleimide functions on mal-HRP at higher pH values and/or increased hydrolysis of 2IT. Both of these processes would reduce the efficiency of conjugation reactions between mal-HRP and thiolated Ab1.

Example 6

The effect of varying pH on conjugation efficiency using mal-GOX was examined as described in Example 5 except that the samples volumes were halved and the reactions were terminated by addition of 975 µl of TBS/0.1% BSA. Samples were analysed by ELISA using rabbit IgG-coated plates (Example 3). Results are shown in FIG. 3.

As can be seen, the pH optimum for conjugating Ab1 and Gox was similar to that seen for the HRP label (Example 5).

Example 7

The effect of varying buffer species at a fixed pH value of 7.4 was examined. Buffer (200 mM) and Ab1 were mixed 1:1 and 10 µl aliquots were dispensed into Eppendorf tubes, followed by 5 µl of 2.5 mg/ml mal-HRP (Example 1) and 5 µl of 5 mM 2IT. Controls reactions were set up with 1.2 mM HCl instead of 2IT. The final concentration of each buffer (Tris, HEPES or sodium phosphate) was 50 mM. Results are shown in FIG. 4.

As can be seen in FIG. 4, conjugations in the presence of either phosphate or HEPES buffer yielded conjugates that showed similar performance by ELISA. Despite the 40-fold molar excess of Tris over 2IT, the absorbancy value for the conjugate prepared in the presence of Tris was reduced by only a factor of ~2. Low absorbance values were seen if 2IT was omitted. In a separate analogous experiment, a conjugate prepared at pH 7.0 in MOPS buffer gave similar ELISA results to a conjugate prepared using sodium phosphate buffer at the same pH (not shown). Thus conjugation reactions may be carried out in several buffers that lack amine functions, and even in the presence of Tris with a modest loss of performance. This effect of Tris is probably explained by amine-induced ring-opening of 2IT (see Example 8) and competition between the free thiols generated and thiolated Ab1 for mal-HRP.

Example 8

The effect of pH on the release of thiols from 2IT was explored using a series of phosphate buffers or Tris buffers. 90 µl samples of each buffer were mixed with 10 µl of 100 mM 2IT and duplicate aliquots (20 µl) were incubated in a clear microplate for 45 min at 25° C. DTNB 200 µl (from 80 µg/ml stock in 200 mM sodium phosphate, 1 mM EDTA, pH 8.0) was added and plates were read at $A_{405}$ after 1 minute. Results are shown in FIG. 5.

As can be seen in FIG. 5, with phosphate buffer the release of thiol becomes more marked as the pH rises, which can be attributed to hydrolysis of 2IT. A pH value of pH 8 or greater is often currently used for thiolation of biomolecules with 2IT. At low pH, 2IT is very stable. For any fixed pH value, the rate of thiol production is greater in the presence of Tris compared with that in the presence of phosphate, which is consistent with the results in Example 7, which showed reduced efficiency of conjugation in the presence of Tris.

Example 9

The rate of conjugate formation in phosphate buffer was examined at three different pH values. 50 μl reactions comprised 10 μl of Ab1 (Example 4), 20 μl of buffer, 10 μl of mal-HRP (Example 1) (2.5. mg/ml) and 10 μl of 1 mM 2IT. At specified time points (5 min, 20 min, 60 min and 2 h) 5 μl samples were withdrawn and diluted 1/200 in TBS/0.1% BSA prior to testing by ELISA with a rabbit IgG coated plate (Example 3). Results are shown in FIG. 6.

As can be seen in FIG. 6, the rate of conjugate production is pH dependent. A steady increase in absorbancy with time is observed for the pH 6.39 and pH 7.14 incubations over the first four hours and two hours, respectively. The initial rate of increase in absorbancy is greatest at pH 8.15 but the rate slows after 20 minutes and absorbancy value for the pH 7.14 incubation overtakes that of the pH 8.15 incubation after 1 hour. Ultimately, the absorbancy value for the low pH incubation also exceeded that for the pH 8.15 incubation (data not shown).

Example 10

HRP (2.5 mg/ml) and buffer (P4; Example 5) (samples 1 through 4) or Ab1 (Example 4) and P4 buffer (samples 9 through 6) were mixed (1:1) and 10 μl portions were mixed with 5 μl of 2IT (1 mM) by staggered addition of 2IT at −30 min, −15 min, −5 min and −1 min, relative to time=0 min, at which point any outstanding materials (either Ab1 or mal-HRP) were added. This allowed in one half of the experiment the formation of thiolated Ab1 prior to the addition of mal-HRP, and in the other half potential polymerisation of mal-HRP prior to the introduction of Ab1. A reference sample (tube 5) was generated with concurrent addition of Ab1 and HRP to 2IT at time=0 min. After a further 60 min of incubation, 975 μl of TBS/0.1% BSA was added and samples were tested by ELISA using a rabbit IgG coated plate (Example 3). Results are shown in FIG. 7.

As can be seen in FIG. 7, the conjugates while not necessarily physically identical, all gave very similar absorbance values by ELISA, which suggests that the order of addition is not critical in this particular experiment. Importantly, the ability to combine mal-HRP and 2IT for significant periods of time without negative effects suggests that the two might easily be combined and lyophilised, in order to allow a simple one-step conjugation procedure in which a solution of the molecule to be labelled is used to reconstitute the lyophilised mixture.

Example 11

Preparation of EDBA-Modified and Ethanolamine-Modified Enzymes

160 μl of sodium periodate (0.1M) was added to 2 ml of HRP (12.5 mg/ml in 0.1M Na phosphate pH 7.2) and incubated in the dark for 25 min at 25° C. The resulting aldehyde-HRP was desalted on Sephadex G-25 to remove excess periodate and reacted with 2,2' (ethylenedioxy)bis-ethylamine ("EDBA" final concentration by volume of 1%) in 0.5M sodium bicarbonate, pH 9.2. After 1 h at RT, sodium cyanoborohydride was added to 50 mM (from 5M stock) to stabilise Schiff bases. After a further 1 h the EDBA-modified HRP sample was desalted into 0.1M sodium phosphate pH 7.2 and adjusted to 5 mg/ml.

Portions of HRP were also modified with ethanolamine (which generates terminal hydroxyls rather than amines) using essentially the same procedure to provide control material, OLA-HRP. EDBA- and OLA-modified HRP typically contained 13 and 2 TNBS-reactive amines, respectively (i.e. provided B-$Y_n$ molecules in which the value of n was, respectively, 13 and 2). Analogous derivatives of Glucose Oxidase (Gox) were prepared with using the same procedure.

EDBA- and OLA-modified HRP (5 mg/ml) were maleimide-activated using 4 mM sulfo-SMCC (as described in Example 1) to generate mal-EDBA-HRP and mal-OLA-HRP, respectively. Samples were desalted into weak buffer (10 mM sodium phosphate pH 7.2) to facilitate subsequent adjustment of pH by addition of more concentrated buffer solutions.

In some experiments, analogous activation reactions were carried out on EDBA-HRP using 4 mM iodoacetic acid succinimidyl ester to introduce iodoacetyl rather than maleimide functions into HRP.

Example 12

Comparison of Mal-EDBA-HRP and Mal-OLA-HRP in Conjugation Reactions

Mal-EDBA-HRP (prepared from two different batches of EDBA-HRP, and mal-OLA-HRP (from Example 11) (10 μl; 25 μg) were each conjugated with 2 μl of 5 mg/ml Goat anti-rabbit IgG (in 200 mM Hepes, pH 7.5) and 1.3 μl of 8 mM TG1. After four hours at 25° C. samples were diluted to 1 ml with TBS/0.1% BSA, from which serial dilutions were prepared and tested in ELISA using either a rabbit IgG coated plate or a control plate (with no rabbit IgG). The results are shown in FIG. 8.

Titration curves for conjugates derived from mal-EDBA-HRP were very similar to one another with OD values in excess of 1.5 at 1/10,000 dilution. By contrast the conjugate prepared with the mal-OLA-HRP required-10-fold higher concentration to achieve similar absorbance values. Data for the control plate (i.e. with no antigen) are superimposed on one another and show baseline readings over the full range of dilutions tested. Thus the strategy of introducing more amine functions prior to maleimide-activation significantly enhances the performance of conjugates in ELISA.

Example 13

Assessment of pH Optimum for Conjugations with Mal-EDBA-HRP

Mal-EDBA-HRP (10 μl) prepared as described above was mixed with 5 μl of 2 mg/ml Goat anti-rabbit IgG (20 mM Na phosphate/150 mM NaCl), 2 ul of TG1 (8 mM) and 3 μl of one of the following 1M buffers: MOPS pH 6.5, MOPS pH 7, Hepes pH 7.5, or EPPS pH 8). After overnight incubation at 25° C., serial dilutions were prepared and tested in ELISA using either a rabbit IgG coated plate or a control plate (with no rabbit IgG). The results are shown in FIG. 9.

A very broad pH optimum was observed in reactions with mal-EDBA-HRP (pH 6.5-7.5) with the conjugate prepared at pH 7 being only marginally better than those prepared at either pH 6.5 or pH 7.5. Thus, addition of extra maleimide functions has the effect of making conjugation reactions more robust to changes in pH compared with reactions carried out with non-diamine treated HRP (compare Example 5).

Example 14

Comparison of Mal-EDBA-Gox and Mal-OLA-Gox in Conjugation Reactions

The applicability of EDBA-treatment in enhancing performance of conjugates is further illustrated with glucose oxidase, which naturally has more available amines than HRP. Nevertheless, periodate oxidation coupled with EDBA treatment affords conjugates that are substantially better than control conjugates (treated with ethanolamine) in which hydroxyls rather than amines are appended.

EDBA-Gox-Ig and OLA-Gox-Ig conjugates were prepared and tested in an ELISA, as described in Examples 11 and 12. The results are presented in FIG. 10.

Example 15

Conjugation Reactions with Iodoacetyl-HRP

Iodoacetyl-EDBA-HRP (prepared as described in Example 11) (10 µl; 25 µg) was conjugated with 2 µl of 5 mg/ml Goat anti-rabbit IgG (in 200 mM Hepes, pH 7.5) and 1.3 µl of 8 mM TG1. After overnight incubation (~16 hours) in the dark at 25° C. the conjugate was diluted to 1 ml with TBS/0.1% BSA, from which serial dilutions were prepared and tested in ELISA using either a rabbit IgG coated plate or a control plate (with no rabbit IgG). The results are shown in FIG. 11.

This illustrates that the methods of the present invention are not limited to electrophilic addition type reactions as exemplified by maleimides but also displacement reactions with haloacetyl derivatives.

Example 16

Effect of Varying Ab:Enzyme Ratio

Either mal-EDBA-HRP or mal-OLA-HRP (10 µl; 25 ug) was mixed with 10 µl of Goat and rabbit IgG of varying concentration (in 200 mM Hepes pH 7.5, and 2 ul of TG1 (8 mM). After 4 h incubation at 25° C., samples were diluted to 250 ng of antibody per ml and tested in ELISA using either a rabbit IgG coated plate or a control plate (with no rabbit IgG). The results are presented in FIG. 12.

As can be seen in FIG. 12, at all antibody:HRP ratios, the conjugates prepared with mal-EDBA-HRP show much higher absorbance values than those prepared with mal-OLA-HRP. The absorbance values are slightly lower with high ratios of antibody to HRP, presumably because the number of HRP molecules attached cannot exceed 2 per molecule of antibody (2:1 weight ratio=~1:2 molar ratio), whereas higher numbers may be attached with lower ratios of antibody to HRP. Thus conjugates of lower molecular weight, which might be advantageous in applications that require penetration into tissues (e.g. as in immunohistochemistry) are favoured by higher antibody:HRP ratios.

It is apparent from FIG. 12 that increasing the ratio of mal-OLA-HRP to Ab (by reducing the amount of antibody in each reaction) has only a modest effect on conjugate performance. Even with a substantial excess of mal-OLA-HRP (16:1 by weight; ~64:1 molar ratio) the efficiency of conjugation never approaches that observed with mal-EDBA-HRP. Since the rate of production of thiolated antibody at any fixed Ab-HRP ratio is the same with both types of HRP some other process must operate to limit conjugation efficiency in the case of excess mal-OLA-HRP. If we consider the more general case of A reacting with B-Y, TG1 reacts with amines on A to generate A-SH. It also reacts with water in a competing hydrolysis reaction, which gets faster with increasing pH, especially above pH 7, to generate unwanted free thiols.

In FIG. 12, since a large excess mal-OLA-HRP gives conjugates that clearly show sub optimal performance, the concentration of unwanted free thiols must reach a critical point (i.e. where conjugation efficiency is compromised) before all of the molecules of Ab-NH$_2$ have been converted into Ab-SH. In the example, the concentration of thiol generator (TG) is 800 µM. The concentration of the amine reactant is ~6 µM (i.e. for 1 mg/ml antibody), or effectively 60 µM amine, (assuming about 10 lysines are capable of reacting with TG). In the case of mal-OLA-HRP the concentration of maleimide functions cannot be any greater than the initial amine content prior to SMCC treatment and is therefore no greater than ~50-100 µM. Although amines are more nucleophilic than water molecules at physiological pH values, the concentrations of reactants and the solvent (i.e. water) are unfavourable in typical conjugation reactions.

Thus merely increasing the ratio of HRP to Ab is not enough to overcome undesirable competing reactions. There have to be sufficient maleimides to cope with a more rapid release of free thiol (i.e. TG hydrolysis) than A-SH production in the conjugation reaction. Although amines on A are more reactive than the hydroxyl groups of water molecules, a very high concentration of water (55 M) is available to attack TG. This underlines why multivalent HRP is especially effective as it can react with unwanted thiols that are generated throughout the 2-3 hours' conjugation reaction and yet still react with A-SH.

Example 17

To investigate various amines as potential quench agents that might be used, if required, to halt conjugation reactions, we examined thiol release from 2IT using a standard DTNB assay. 5 mM solutions of glycine, ethanolamine, or 1,3-diaminopropane (DAP) were prepared in 100 mM sodium phosphate buffer, pH 7.4. 980 µl aliquots of each buffer were mixed with 20 µl of 100 mM 2IT in 1.2 mM HCl. Freshly prepared DTNB reagent (200 µl of 80 µg/ml solution in 10 mM sodium phosphate, 1 mM EDTA, pH 8.0) was added to 20 µl aliquots of each reaction mix over a time course. Samples were read within 1 minute of DTNB addition. Results are shown in FIG. 13.

The amines that were selected, ethanolamine, glycine and DAP, additionally contain neutral, acidic, and basic groups, respectively. It is important to note that the data in FIG. 14 potentially represent the net effect of two opposing pathways (i) thiol release from 2IT (ii) intramolecular reaction of released thiol. This is particularly evident with glycine where the amount of thiol begins to fall after one hour. The highest 'apparent' rate is with DAP, but despite its extra amine function compared with glycine or ethanolamine this appears not to explain greater thiol release (see Example 18) but rather a slower intramolecular reaction, which is perhaps connected with the extra positive charge that is introduced into the product of the initial ring-opening reaction.

Example 18

To get a better appreciation of the initial rates of thiol release with potential quenchers, the experiment of Example 17 was modified to allow immediate 'capture' of any released thiol by reaction with DTNB. Because of the need to measure DTNB reactions at pH 8, it was not possible to use the same pH as in Example 17, but the same three amines were studied. DTNB (80 μg/ml) was freshly prepared in 0.2M sodium phosphate, 1 mM EDTA, pH 8.0, and dispensed (200 μl per well) into a clear 96-well plate. 20 μl of 100 mM 2IT was added and the absorbancy was read at $A_{405}$ every 2 min using an automatic plate cycling function. Results are shown in FIG. 14.

As can be seen in FIG. 14, the three amines induce the release of thiols at very similar rates, though glycine is the fastest. Since glycine also appears to support a relatively fast intramolecular reaction that leads to disappearance of thiols (Example 17), it is the most promising of the three amines for halting conjugation reactions. A significant release of thiols under conditions normally used for thiolation of biomolecules (i.e. the control reaction in this experiment) is also evident.

Example 19

Freeze-drying is commonly employed to stabilize and extend the shelf life of protein-based products. Excipients that are often used to help to stabilize the active constituents include cryoprotectants, whose primary function is to afford protection during the freezing step, and lyoprotectants, whose function is to prevent degradation during freeze drying and/or during storage. For any new sample, the best formulation for freeze-drying can only be determined empirically. There are no precedents, as far as we are aware, for freeze-drying of TG or for freeze-drying of TG in the presence of B-Y molecules. Freeze-drying of mixtures of TG and B-Y requires the development of a single formulation to stabilize Y functions (e.g. maleimides), TG (e.g. 2-IT) and the biological activity of B (e.g. HRP, alkaline phosphatase). Clearly, if there is significant damage to one active ingredient any subsequent conjugation reactions will be compromised even if the other components are well preserved.

In initial experiments with a range of buffers of varying composition and pH, the extent of unwanted ring opening of 2-IT (alone) during freeze drying was assessed by measuring free thiol content of the freeze-dried material using DTNB reagent. The release of free thiols appeared to be dependent on the pH of the solution prior to freeze-drying. Acidic solutions, including dilute hydrochloric acid (1.2 mM-12 mM), 20 mM sodium phosphate (pH<6.5) and 20 mM sodium acetate (pH 5) gave freeze-dried materials with low free thiol content, consistent with the previously noted greater solution stability of 2-IT at low pH (Example 8). Buffers commonly used for conjugation reactions (i.e. those based on neutral or slightly basic solutions of phosphate, NaCl and EDTA) were relatively poor stabilizers of 2-IT in freeze-drying, as were other buffers of pH>6.5.

An unexpected observation was made when the freeze-dried 2-IT samples were left incubating with DTNB reagent for several hours. Normally, because 2-IT is unstable at the pH used for the DTNB reaction (pH 8), there is a time-dependent release of thiols, and thus a rising background signal. Despite the apparent stabilization of 2-IT in sodium acetate (i.e. absence of thiols after free-drying), the expected time-dependent increase in the background signal was largely absent. This observation was not explained by any direct inhibitory effect of acetate on the reaction of DTNB with thiols. The presumed chemical transformation of TG1 that prevented the release of thiol groups was not further investigated, but it may be similar to the secondary reaction observed under other conditions for TG1 (see p 4), which leads to the formation of a unreactive thioether. Conjugates prepared with mal-HRP/TG1 mixtures that were freeze dried in the presence of 4 mM sodium phosphate, pH 5.8, gave far stronger signals in ELISA than those freeze dried in the presence of 5 mM sodium acetate pH 5. Taken together the results illustrate that while low pH is necessary for stabilization of TG1 during freeze-drying (and thus for efficient conjugate formation subsequently carried out at slightly alkaline pH), a low pH alone is not sufficient to preserve the integrity of TG1.

In a preferred embodiment of the present invention the buffer for freeze-drying mixtures of B-Y/TG1 comprises sodium phosphate. The pH of the buffer is preferably below 6.5 and more preferably below 6.0.

As it is necessary to raise the pH of the freeze-dried mixture upon reconstitution with a buffered solution of A in order to provide optimal conditions for bioconjugation reactions, weakly buffered freeze-dried mixtures are preferred. Preferably the buffer concentration is below 200 mM; more preferably below 50 mM and most preferably below 20 mM.

In a preferred embodiment of the present invention, the mixture of freeze-dried TG/B-Y/phosphate buffer also contains a polyol, such as a sugar or dextran, or combinations of polyols. Most preferably the polyol is trehalose. The concentration of trehalose is preferably >1%, and most preferably around 5% (w/v).

In a particularly preferred embodiment, where B-Y is either HRP or alkaline phosphatase, the mixture also contains a metal ion or metal ions. In a particularly preferred embodiment the metal ion is $Ca^{2+}$ or $Mg^{2+}$ (typically added as $MgCl_2$), preferably in the range 1-10 mM $Mg^{2+}$, desirably about 5 mM.

Example 19.1

Freeze Drying of Maleimide-Activated Enzymes with 2-IT

Alkaline phosphatase (16.2 mg/ml; Biozyme code ALP112G) in 5 mM Tris/5 mM $MgCl_2$/0.1 mM $ZnCl_2$, pH 7.0 was diluted to 5 mg/ml with 0.1M sodium phosphate pH 7.2 and activated with 4 mM sulfo-SMCC for 1 h at 25° C. The sample was then desalted into 10 mM sodium phosphate pH 5.8 to give a concentration of 3.125 mg/ml. 2. Excipients were added, as required, and 2-IT was added last typically at 400 or 800 μM concentration. The final concentration of enzyme prior to freeze drying was 2.5 mg/ml. Samples were rapidly frozen in liquid nitrogen in polypropylene tubes or glass vials prior to freeze drying in an Advantage ES freeze dryer using a 24 hour cycle: Step 1, shelf temperature −40° C. for 1320 minutes, step 2 shelf temperature −10° C. for 60 minutes and step 3 shelf temperature +20° C., 60 minutes. Following freeze-drying, samples were stored at either −20 or 37° C. for several days.

EDBA-modified HRP was prepared as in Example 11, and activated with SMCC as described above. The sample was desalted as described above into 10 mM sodium phosphate pH 5.8 and further prepared for freeze-drying as described for alkaline phosphatase.

Example 20

Stability of Freeze Dried Mal-HRP/2-IT Mixtures

Maleimide-activated EDBA-modified HRP was desalted into pH 5.8 buffer (as described above, Example 19) and TG1 was added to give a final concentration of 800 µM prior to freeze-drying of 40 µl portions (100 µg HRP). 320 µl of 1 mg/ml Goat anti-mouse IgG antibody in 20 mM sodium phosphate/150 mM NaCl, pH 7.2, was supplemented with 32 µl of 2M Hepes/10 mM EDTA, pH 7.25. 100 µl of this material was used to reconstitute each vial of the freeze-dried mixture. Conjugation was allowed to proceed at 25° C. overnight and the resulting conjugates were tested by ELISA on a mouse IgG-coated plate prepared as described in Example 3.

The results are illustrated in FIG. 15, which is a graph of absorbancy at 405 nm (in arbitrary units) against a log scale of conjugate dilution. The graph shows the titration of conjugates prepared as described in this example using lyophilised mixtures which were incubated overnight, prior to conjugation, at −20° C. (solid circles), 25° C. (open circles) or 37° C. (solid squares).

As can be seen, as the lyophilized mixture is subjected to increasing temperature there is a marked loss of performance of the resulting conjugates. At 1/10,000 dilution the absorbance signal for conjugate prepared with mixture stored overnight at 37° C. is ~20% of that for the conjugate prepared with mixture stored at −20° C., and the dilution of conjugate required to give an absorbance of 1.0 is shifted by an order of magnitude.

Example 21

Stabilization of Freeze Dried Mal-Enzyme/2-IT

Sugars often help to stabilize proteins during freeze drying and/or storage, and the inclusion of trehalose in freeze-dried mixtures of maleimide-EDBA-HRP/TG and maleimide-alkaline phosphatase/TG at 37° C. significantly increased stability compared with samples lacking the sugar (as measured by performance in ELISA of conjugates prepared from the mixtures) (see Table below and Example 20). Since alkaline phosphatase is commonly assayed in the presence of $Mg^{2+}$ and $Zn^{2+}$ ions we considered the possibility that metal ions might further help to stabilize this enzyme during freeze-drying or storage. However, since metal ions might have damaging effects on other components (e.g. 2-IT) during freeze-drying, or might interfere with subsequent conjugation reactions, we performed some initial trials using HRP, which is less expensive than alkaline phosphatase.

Freeze dried mixtures were prepared as described in Example 19 containing malemide-activated EDBA-modified HRP in 10 mM sodium phosphate buffer, pH 5.8, plus trehalose 5% (w/v), metal ions (as noted below), and 2-IT (400 µM). Mixtures were stored at 37° C. prior to conjugation. To our surprise, for HRP samples that were spiked with 5 mM $MgCl_2$ (which is not required for activity of HRP) and then freeze-dried, the stability at 37° C. of the freeze-dried mixture markedly improved, as judged by performance in ELISA of Goat anti-rabbit IgG-HRP conjugates prepared with the mixture, and tested as described in Example 3. In subsequent studies with trehalose/2-IT/maleimide-alkaline phosphatase mixtures, we found that $MgCl_2$ had not only a protective action on alkaline phosphatase during storage at elevated temperature but also a cryoprotective action. These results and those for other metal ions are summarized in the table below.

Stabilization of Mal-EDBA-HRP/2-IT and Mal-Alkaline Phosphatase/2-IT Mixtures at 37° C. as Measured by Conjugate Performance in ELISA

| Enzyme | Additive | % Trehalose (−20° C.) |
|---|---|---|
| Mal-EDBA-HRP | Trehalose | 25 |
| Mal-EDBA-HRP | Trehalose/$Mg^{2+}$ (5 mM) | 77 |
| Mal-EDBA-HRP | Trehalose/$Zn^{2+}$ (0.5 mM) | 34 |
| Mal-EDBA-HRP | Trehalose/$Ca^{2+}$ (5 mM) | 84 |
| Mal-alkaline phosphatase | Trehalose | 37 |
| Mal-alkaline phosphatase | Trehalose/$Mg^{2+}$ (5 mM) | 104 |
| Mal-alkaline phosphatase | Trehalose/$Zn^{2+}$ (0.5 mM) | 44 |
| Mal-alkaline phosphatase | Trehalose/$Mg^{2+}$ (5 mM)/ $Zn^{2+}$ (0.5 mM) | 102 |
| Mal-alkaline phosphatase | Trehalose/$Mg^{2+}$ (5 mM) | 148* |

*$Mg^{2+}$/trehalose at −20° C. versus trehalose at −20° C.

Freeze-dried mixtures were incubated at 37° C. for 6 days (HRP) or 5 days (alkaline phosphatase) and then used to prepare goat anti-rabbit conjugates that were tested in a rabbit IgG ELISA. The % activity values were determined by dividing the ELISA absorbance value for a 1/10,000 dilution of conjugate prepared from material stored at 37° C. by the absorbance value obtained for a trehalose formulation (i.e. with no metal ions) prepared from material stored at −20° C., unless otherwise stated.

As can be seen, trehalose improves the stability of the mixture to elevated temperature (the 75% loss of activity over 6 days [$1^{st}$ line of the table] is broadly similar to that over 1 day without trehalose; see Example 20). $Mg^{2+}$ further significantly improves the stability of mal-EDBA-HRP/2-IT/trehalose mixtures, and there is only a 23% loss of activity following incubation for 6 days at 37° C. of the freeze-dried mixture that was used to prepare conjugate. In respect of a conjugation kit comprising freeze-dried materials, the formulation with trehalose and $Mg^{2+}$ greatly facilitates transportation at ambient temperatures. Calcium (5 mM) also stabilized mal-EDBA-HRP/2-IT/trehalose mixtures, but $Zn^{2+}$ at concentrations commonly employed in assays of alkaline phosphatase (0.5 mM) had little protective effect.

A similar pattern emerges with alkaline phosphatase, with a marked improvement in the ELISA reactivity of resulting conjugates if the mal-alkaline phosphatase/2-IT mixture is freeze dried in presence of trehalose and $Mg^{2+}$. Compared with formulations containing trehalose alone and stored at −20° C., there is apparently no loss of activity after 5 days of storage at 37° C. Unlike HRP, however, where the beneficial effect of the excipients is seen at elevated temperature, rather than during freeze-drying, mal-alkaline phosphatase/2-IT mixtures are also protected by the excipients during freezing/freeze-drying. Thus, samples freeze-dried in the presence of $Mg^{2+}$ are substantially more active immediately after freeze drying than those in the absence of the metal ion.

The invention claimed is:

1. A method of reacting a polypeptide first chemical entity and an enzyme or fluorescent material second chemical entity to form a conjugate in which the first and second chemical entities are covalently bound with respect to each other, comprising the steps of forming a conjugation reaction mixture by bringing into simultaneous contact in aqueous conditions, the first chemical entity, the second chemical entity and a thiol generator, wherein the thiol generator reacts with the polypeptide first chemical entity in a thiolation reaction resulting in formation of a free sulfhydryl group on the polypeptide first chemical entity, wherein reaction of the thiol generator with a primary amine on the polypeptide first chemical entity takes place at a pH below 8, and the free sulfhydryl group reacts with the enzyme or fluorescent second chemical entity to form the conjugate, and wherein the enzyme or fluorescent second chemical entity is modified by the attachment of at least two molecules that bind sulfhydryl groups and is therefore polyvalent with respect to its reactivity with sulfhydryl groups, and further wherein the molar ratio of the enzyme or fluorescent second chemical entity to thiol generator is 1:1 or less.

2. The method according to claim 1, wherein the thiol generator comprises one or more of a thiolactone, an iminothiolactone, an episulfide and a thiazolidine.

3. The method according to claim 2, wherein the thiol generator comprises 2-iminothiolane.

4. The method according to claim 1, wherein the polypeptide first chemical entity, the enzyme or fluorescent material second chemical entity and the thiol generator are combined simultaneously in a one step procedure.

5. The method according to claim 1, comprising a first step in which the thiol generator and the polypeptide first chemical entity are combined, and a second step in which the enzyme or fluorescent material second chemical entity is combined with the thiol generator and first chemical entity.

6. The method according to claim 1, comprising a first step in which the polypeptide first and enzyme or fluorescent material second chemical entities are combined, and a second step in which the thiol generator is combined with the polypeptide first and enzyme or fluorescent material second chemical entities.

7. The method according to claim 1, comprising a first step in which the thiol generator and enzyme or fluorescent material second chemical entity are combined, and a second step in which the polypeptide first chemical entity is combined with the thiol generator and the enzyme or fluorescent material second chemical entity.

8. The method according to claim 7, wherein the polypeptide first chemical entity is added in liquid form to a dried mixture comprising the enzyme or fluorescent material second chemical entity and the thiol generator.

9. The method according to claim 1, wherein the thiol generator has a free thiol group content of less than 5% in molar terms.

10. The method according to claim 1, wherein the thiol generator is present in up to 120 times molar excess in relation to the polypeptide first chemical entity.

11. The method according to claim 1, wherein the enzyme or fluorescent material second chemical entity is present in up to 10 times molar excess in relation to the polypeptide first chemical entity.

12. The method according to claim 1, wherein the enzyme or fluorescent material second chemical entity comprises a polymer.

13. The method according to claim 1, wherein the enzyme or fluorescent material second chemical entity comprises a polypeptide.

14. The method according to claim 1, wherein the enzyme or fluorescent material second chemical entity comprises an enzyme.

15. The method according to claim 1, wherein the enzyme or fluorescent material second chemical entity comprises a molecule selected from the group consisting of: horseradish peroxidase, alkaline phosphatase and glucose oxidase.

16. The method according to claim 1, wherein the enzyme or fluorescent material second chemical entity comprises five or more sulfhydryl-reactive groups per molecule.

17. The method according to claim 1, wherein the enzyme or fluorescent material second chemical entity comprises ten or more sulfhydryl-reactive groups per molecule.

18. The method according to claim 1, wherein the enzyme or fluorescent material second chemical entity comprises from five to fifteen sulfhydryl-reactive groups per molecule.

19. The method according to claim 1, wherein the molar ratio of second chemical entity to thiol generator is less than 1:1.

20. The method according to claim 19, wherein the molar ratio is of second chemical entity to thiol generator in the range 1:1 to 1:20.

21. The method according to claim 19, wherein the molar ratio of second chemical entity to thiol generator is in the range 1:10 to 1:15.

22. The method according to claim 1, wherein reaction of the thiol generator with a primary amine on the polypeptide first chemical entity takes place at a pH below 7.8.

23. The method according to claim 1, wherein the reaction of the thiol generator with a primary amine on the polypeptide first chemical entity takes place at a pH below 7.7.

24. The method according to claim 9, wherein the thiol generator has a free thiol group content of less than 3% in molar terms.

25. The method according to claim 9, wherein the thiol generator has a free thiol group content of less than 1% in molar terms.

26. The method according to claim 1, further comprising adding a nucleophile to terminate the conjugation reaction.

27. A method of reacting a polypeptide first chemical entity and an enzyme or fluorescent material second chemical entity to form a conjugate in which the first and second chemical entities are covalently bound with respect to each other, comprising the steps of forming a conjugation reaction mixture by bringing into simultaneous contact in aqueous conditions, the first chemical entity, the second chemical entity and a thiol generator, wherein the thiol generator reacts with the polypeptide first chemical entity in a thiolation reaction resulting in formation of a free sulfhydryl group on the polypeptide first chemical entity, and the free sulfhydryl group reacts with the enzyme or fluorescent second chemical entity to form the conjugate, and wherein the enzyme or fluorescent second chemical entity is polyvalent with respect to its reactivity with sulfhydryl groups, and further wherein the molar ratio of the enzyme or fluorescent second chemical entity to thiol generator is 1:1 or less; and terminating the formation of the conjugate by adding a nucleophile to the conjugation reaction mixture.

* * * * *